United States Patent
Sharma

(10) Patent No.: US 10,179,239 B2
(45) Date of Patent: Jan. 15, 2019

(54) PERSONALIZED PAIN MANAGEMENT TREATMENTS

(71) Applicant: iTrace Biomedical Inc., Milpitas, CA (US)

(72) Inventor: Krishnamohan Sharma, Milpitas, CA (US)

(73) Assignee: ITRACE BIOMEDICAL INC., Milpitas, CA (US)

(*) Notice: Subject to any disclaimer, the term of this patent is extended or adjusted under 35 U.S.C. 154(b) by 0 days.

(21) Appl. No.: 15/079,678

(22) Filed: Mar. 24, 2016

(65) Prior Publication Data

US 2016/0243359 A1    Aug. 25, 2016

Related U.S. Application Data

(63) Continuation of application No. 15/021,143, filed as application No. PCT/US2016/015984 on Feb. 1, (Continued)

(30) Foreign Application Priority Data

Jan. 15, 2013  (IN) .............................. 199/CHE/2013

(51) Int. Cl.
*A61N 7/00*    (2006.01)
*A61N 1/00*    (2006.01)
(Continued)

(52) U.S. Cl.
CPC ............ *A61N 1/36021* (2013.01); *A61F 7/00* (2013.01); *A61F 7/007* (2013.01); *A61F 7/08* (2013.01);
(Continued)

(58) Field of Classification Search
CPC ........ A61B 5/6833; A61B 2017/00172; A61B 2018/00791; A61B 2562/0295;
(Continued)

(56) References Cited

U.S. PATENT DOCUMENTS 4,286,592 A    9/1981    Chandrasekaran
4,404,460 A    9/1983    Kerr
(Continued)

OTHER PUBLICATIONS

International Patent Application No. PCT/US2016/015984, International Search Report and Written Opinion Received dated Apr. 18, 2016, 14 pages.
(Continued)

*Primary Examiner* — Elmer Chao
(74) *Attorney, Agent, or Firm* — Kilpatrick Townsend & Stockton LLP

(57) ABSTRACT

Systems and methods disclosed herein provide efficacious pain management therapies based on delivery of physical medicine(s) via computer-implemented systems. Patient information comprising patient pain symptoms, patient physiological measurements, patient demographics, and other information is received at a pain therapy device. The patient information is compared with pain analytics data compiled on a plurality of individuals to determine a personalized pain management therapy. The personalized pain management therapy is applied via a combination of thermoceuticals, electroceuticals, ultrasound, and several other forms of physical medicine. Sensors coupled to the pain therapy device measure changes in physiological data resulting from the pain management therapy. The personalized pain management therapy can be adjusted based on the changes in the physiological data and/or patient feedback. The patient information, information about the applied therapy, and therapy outcome information is added to the analytics database.

14 Claims, 12 Drawing Sheets

Related U.S. Application Data 2016, now Pat. No. 9,875,340, application No. 15/079,578, which is a continuation-in-part of application No. 14/011,273, filed on Aug. 27, 2013, now Pat. No. 9,710,607.

(60) Provisional application No. 62/110,017, filed on Jan. 30, 2015.

(51) Int. Cl.

| | | |
|---|---|---|
| *A61N 1/36* | (2006.01) | |
| *A61F 7/08* | (2006.01) | |
| *A61F 7/10* | (2006.01) | |
| *A61N 5/06* | (2006.01) | |
| *A61N 5/02* | (2006.01) | |
| *A61F 7/00* | (2006.01) | |
| A61M 37/00 | (2006.01) | |
| A61F 7/02 | (2006.01) | |

(52) U.S. Cl.
CPC .............. *A61F 7/10* (2013.01); *A61N 5/025* (2013.01); *A61N 5/0625* (2013.01); *A61N 7/00* (2013.01); *A61F 2007/0071* (2013.01); *A61F 2007/0075* (2013.01); *A61F 2007/0078* (2013.01); *A61F 2007/0093* (2013.01); *A61F 2007/0095* (2013.01); *A61F 2007/029* (2013.01); *A61F 2007/108* (2013.01); *A61M 37/0092* (2013.01); *A61N 2005/0659* (2013.01); *A61N 2007/0008* (2013.01); *A61N 2007/0013* (2013.01); *A61N 2007/0017* (2013.01)

(58) Field of Classification Search
CPC ... A61M 37/0092; A61N 5/0625; A61N 7/00; A61N 5/025; A61N 1/36021; A61N 2005/0659; A61N 2007/0008; A61N 2007/0013; A61N 2007/0017; A61F 7/08; A61F 7/10; A61F 7/00; A61F 7/007; A61F 2007/108; A61F 2007/0071; A61F 2007/0075; A61F 2007/0078; A61F 2007/0093; A61F 2007/0095; A61F 2007/029

See application file for complete search history.

(56) References Cited

U.S. PATENT DOCUMENTS

| | | | |
|---|---|---|---|
| 4,736,088 A | | 4/1988 | Bart |
| 4,823,775 A | | 4/1989 | Rindt |
| 5,036,861 A | | 8/1991 | Sembrowich et al. |
| 5,076,273 A | | 12/1991 | Schoendorfer et al. |
| 5,139,023 A | | 8/1992 | Stanley et al. |
| 5,140,985 A | | 8/1992 | Schroeder et al. |
| 5,279,543 A | | 1/1994 | Glikfeld et al. |
| 5,413,550 A | * | 5/1995 | Castel ............... A61H 23/0245 601/2 |
| 5,421,816 A | | 6/1995 | Lipkovker |
| 5,658,247 A | | 8/1997 | Henley |
| 5,667,487 A | | 9/1997 | Henley |
| 5,697,896 A | | 12/1997 | McNichols et al. |
| 5,722,397 A | | 3/1998 | Eppstein |
| 5,833,647 A | | 11/1998 | Edwards |
| 5,860,857 A | | 1/1999 | Wasastjerna et al. |
| 5,860,957 A | | 1/1999 | Jacobsen et al. |
| 5,902,603 A | | 5/1999 | Chen et al. |
| 5,935,598 A | | 8/1999 | Sage et al. |
| 5,947,921 A | | 9/1999 | Johnson et al. |
| 5,948,012 A | | 9/1999 | Mahaffey et al. |
| 6,142,939 A | | 11/2000 | Eppstein et al. |
| 6,180,416 B1 | | 1/2001 | Kurnik et al. |
| 6,190,315 B1 | | 2/2001 | Kost et al. |
| 6,251,083 B1 | | 6/2001 | Yum et al. |
| 6,261,595 B1 | | 7/2001 | Stanley et al. |
| 6,334,856 B1 | | 1/2002 | Allen et al. |
| 6,527,716 B1 | | 3/2003 | Eppstein |
| 6,572,871 B1 | | 6/2003 | Church et al. |
| 6,623,457 B1 | | 9/2003 | Rosenberg |
| 6,649,886 B1 | | 11/2003 | Kleshchik |
| 6,662,044 B2 | | 12/2003 | Crawford et al. |
| 6,692,456 B1 | | 2/2004 | Eppstein et al. |
| 7,483,738 B2 | | 1/2009 | Tamarkin et al. |
| 7,650,177 B2 | | 1/2010 | Hoarau et al. |
| 9,327,105 B2 | | 5/2016 | Ramdas et al. |
| 2002/0055702 A1 | | 5/2002 | Atala et al. |
| 2002/0114827 A1 | | 8/2002 | Zhang et al. |
| 2002/0156415 A1 | | 10/2002 | Redding, Jr. |
| 2003/0023151 A1 | | 1/2003 | Khalil et al. |
| 2003/0032900 A1 | | 2/2003 | Ella et al. |
| 2003/0100846 A1 | | 5/2003 | Custer et al. |
| 2003/0208113 A1 | | 11/2003 | Mault et al. |
| 2003/0225360 A1 | | 12/2003 | Eppstein et al. |
| 2004/0073079 A1 | | 4/2004 | Altshuler et al. |
| 2004/0210214 A1 | * | 10/2004 | Knowlton ............ A61B 18/14 606/41 |
| 2005/0283110 A1 | | 12/2005 | Atala et al. |
| 2006/0058709 A1 | * | 3/2006 | Mason .................. A61N 7/00 601/2 |
| 2007/0083186 A1 | | 4/2007 | Carter et al. |
| 2007/0265664 A1 | | 11/2007 | Gerber et al. |
| 2009/0069041 A1 | | 3/2009 | Kitazoe |
| 2010/0081971 A1 | * | 4/2010 | Allison ................ A61B 34/10 601/2 |
| 2010/0114252 A1 | | 5/2010 | Torgerson |
| 2010/0217349 A1 | | 8/2010 | Fahey et al. |
| 2011/0264028 A1 | | 10/2011 | Ramdas et al. |
| 2013/0079605 A1 | | 3/2013 | Bandaru et al. |
| 2014/0200487 A1 | | 7/2014 | Ramdas et al. |
| 2014/0244292 A1 | | 8/2014 | Rosenberg et al. |
| 2014/0343628 A1 | | 11/2014 | Kaula et al. |
| 2016/0350509 A1 | | 12/2016 | Sharma |

OTHER PUBLICATIONS

Park et al., The effect of heat on skin permeability, International Journal of Pharmaceutics, vol. 359, No. 1-2, Jul. 9, 2008, pp. 94-103.
U.S. Appl. No. 14/011,273, Response to Non-Final Office Action dated Oct. 29, 2015, 20 pages.
U.S. Appl. No. 14/011,273, Non-Final Office Action dated Aug. 31, 2015, 10 pages.
Ingraham, Paul; "Does Therapeutic Ultrasound Work?" updated Mar. 4, 2017 (first published 2009); https://www.painscience.com/articles/ultrasound.php as accessed from the internet Mar. 21, 2017.
"Pain Relief Now", Watch, Comment & Share at ConsumerReports.org; Jun. 2016; pp. 28-36.
U.S. Appl. No. 14/011,273, Final Office Action dated Mar. 24, 2016.
U.S. Appl. No. 14/011,273, Response to Final Office Action and filing of Request for Continued Examination dated May 24, 2016.
U.S. Appl. No. 14/011,273, Non-Final Office Action dated Aug. 19, 2016.
U.S. Appl. No. 14/011,273, Response to Non-Final Office Action dated Nov. 4, 2016.
U.S. Appl. No. 14/011,273, Final Office Action dated Jan. 6, 2017.
U.S. Appl. No. 14/011,273, Response to Final Office Action dated Mar. 6, 2017.
U.S. Appl. No. 14/011,273, Notice of Allowance dated May 8, 2017.
U.S. Appl. No. 15/021,143, Non-Final Office Action dated Jan. 9, 2017, 15 pages.
U.S. Appl. No. 15/021,143, "Notice of Allowance", dated Sep. 22, 2017, 5 pages.

\* cited by examiner

PERSONALIZED PAIN MANAGEMENT TREATMENTS

CROSS REFERENCE TO RELATED APPLICATIONS

This application is a continuation of U.S. application Ser. No. 15/021,143, filed Mar. 10, 2016, titled "Personalized Pain Management Treatments," which application is the U.S. national phase entry of International Patent Application No. PCT/US16/15984 filed on Feb. 1, 2016 and titled "Personalized Pain Management Treatments," which application claims priority to U.S. Provisional Application Ser. No. 62/110,017, filed on Jan. 30, 2015 and titled "Devices, Systems, and Methods for Pain Management," the contents of each of which are hereby incorporated by reference. This application is also a continuation-in-part of application Ser. No. 14/011,273, filed Aug. 27, 2013 (published as Patent Publication No. US 2014/0200487) and titled "Portable Electronic Therapy Device and Method Thereof," the contents of which are hereby incorporated by reference.

TECHNICAL FIELD

This disclosure provides a portable, electronic therapy device that is capable of delivering physical modalities involving different kinds of thermal, electrical ultrasonic energies to stimulate human/animal body for therapeutic purposes. The therapy device can include automatic controlled application of energies along with feedback control using sensors for improved synergistic effects. The device can be used for pain management, healing, fitness, cosmetic and topical delivery related applications. This disclosure further relates to computer-implemented methods and systems for health care management, and more specifically relates to computer-implemented pain management treatment using the disclosed therapy device or other therapy devices. The methods and systems provide improved uses for devices configured to deliver pain management therapies.

BACKGROUND

An individual with a disease, particularly a chronic disease, may be required to monitor various health parameters on a regular basis in support of any treatment or therapy that he or she is undergoing or receiving. Today, advances in medical research enable a range of therapeutic options to treat a given disease, or ailment and/or their symptoms, where each of the proposed therapies targets a particular biochemical or physiochemical process underlying or associated with the disease to provide either a cure or relief from the disease symptoms. For example, if one were to consider various options available for treating pain symptoms, the possible diagnoses medicaments and therapies are many. It is possible that the therapy/medication a patient receives could be subjective and depend upon the particular doctor/physician, i.e., his/her background, expertise and past experiences. For example, a physiotherapist or an orthopedic physician may treat a pain symptom differently than a physician or pain management specialist. Although a doctor plays a critical role in diagnosing and prescribing the therapy, the patient (and his/her family members or care givers) also has great responsibility in complying with the prescription, and following the course of action for achieving improved health and better quality of life. However, unfortunately, depending upon the patient demographics and nature of the disease, health care management of pain management and implementation of pain management has become a daunting task and an expensive affair.

For example, of the all diseases, chronic pain is one of the most underestimated health care problems in the world today, causing major consequences for the quality of life of the patients and the family members and has been a major burden on the health care system. The most common causes of chronic pain are musculoskeletal problems (fractures, dislocations, soft injuries) and inflammatory conditions, with back pain and arthritis pain symptoms accounting for a significant portion of the overall chronic pain population. The four most common ways to treat pain are: (1) pharmaceutical (e.g., analgesics, aspirin; NSAIDs, Ibuprofen, COX-2 inhibitors, celecoxib; opioids, morphine), (2) procedural (neuro-stimulators, pulsed radiofrequency, intrathecal), (3) psychological (behavioral, cognitive), and (4) physical (e.g., heat, cold, transcutaneous electric nerve simulation (TENS), therapeutic ultrasound, infrared, microwave or shortwave diathermy, electro-magnetic radiation, acupuncture, massage). Although pharmaceutical methods (e.g., drugs) are most widely used for treating pain, individuals on over the counter or prescription drugs for pain are frequently dissatisfied with the results of the pharmaceutical treatment. Further, the adverse side effects that drugs may cause on prolonged usage is shifting the focus away from drugs toward alternate methods for managing chronic pain. The procedural methods are invasive, expensive and their effectiveness has been difficult to quantify. Psychological therapies often lack practicality and their success rates have been limited. Finally, physiotherapy based methods have been proven attractive, but they are inconvenient, require bulky/complex instruments, and regular office/hospital visits, all of which lowers compliance. In addition, these therapies are often not supported by quality clinical data despite tremendous advances made in understanding pathophysiology and pain signaling.

Although, a number of physical medicine/modalities based therapies have been administered to treat musculoskeletal pain, identifying the optimal therapy and dosage for pain symptoms has been elusive. For example, clinical data published in the literature indicates that the application of physical medicine is appropriate/beneficial in some cases and not so beneficial in other cases. The response from patients to these methods is similarly mixed. Given this background, the patient (or his/her doctor) has no way of knowing what is the best treatment method. If one were to consider the combined use of these the application of physical therapies, the possible variations may be several (including dosage, therapy session and duration), but combination therapies may provide an opportunity to fine the therapy to make it efficacious or even personalized, especially when one takes advantage of modern technological advances such as computing, internet of things, sensing, connectivity, big data, and analytics in conjunction with electronic medication/therapy.

Therefore, there exists a need for a medical device and an associated system for offering improved therapies for sustained pain relief that takes into account objective and subjective patient feedback and further takes into account the statistical certainty of obtaining a satisfactory outcome.

SUMMARY

The present disclosure provides a method and system for providing efficacious, personalized, pain management therapies. A patient is provided with a pain therapy device capable of delivering individual, or multiple or combination physical therapies accompanied with a computer-implemented system that automatically or manually adjusts the applied pain management treatment based on physiological responses and/or user feedback. Physical therapies can be applied using a combination of thermoceuticals (e.g., temperature application based therapies such as surface heating/cooling using heat pack or cold packs or microwave/shortwave/ultrasound/infra red/laser radiation based thermal therapies, contrast therapies), or combination of thermoceuticals and electroceuticals (e.g., electrical stimulation based therapies such as TENS), or a combination of these treatments with ultrasound. Ultrasound, when applied in pulses, can produce non-thermal effects (acoustic streaming, cavitation) and facilitates healing in the inflammatory and proliferative phase following soft tissue injury, increases local circulation because of the increased capillary density, and bone healing.

In some embodiments, physical therapies can also be administered by including infrared heating or electromagnetic radiation or radio frequency ablation. Physiological responses may be measured via one or more sensors that measure blood flow, blood oxygen levels, tissue thickness or superficial or deep tissue temperatures or other physiological metrics that are associated with pain symptoms. Upon applying a pain management therapy, the pain therapy device can receive updated physiological responses and adjust the pain therapy applied until physiological responses and/or user feedback indicate a satisfactory pain management outcome.

In additional embodiments, the computer-implemented system identifies a correlation between the patient information (e.g., patient demographics, pain symptoms, applied treatment options, and/or treatment outcomes) and analytics data compiled on a plurality of individuals. The analytics data tracks historical data on previous patients, treatments applied, and treatment outcomes. The analytics data can indicate for example, a treatment option that was previously applied to patients with similar demographic information and a statistical likelihood that the therapy option results in satisfactory pain relief. The pain therapy device can receive the identified treatment option from the analytics data and adjust the applied treatment to match the identified treatment option. The computer-implemented system can further store pain the patient information and the applied pain management treatment in a database, thereby adding to the analytics data.

The disclosed device, methodology and intelligent pain management algorithm together provide a powerful tool for managing pain efficiently and effectively. Embodiments herein further relieve patients of the burden of having to try a plethora of devices or other treatment modalities in search of finding relief from pain.

These illustrative embodiments are mentioned not to limit or define the disclosure, but to provide examples to aid understanding thereof. Additional embodiments are discussed in the Detailed Description, and further description is provided there.

BRIEF DESCRIPTION OF THE FIGURES

These and other features, embodiments, and advantages of the present disclosure are better understood when the following Detailed Description is read with reference to the accompanying drawings.

DETAILED DESCRIPTION

Figure 1:
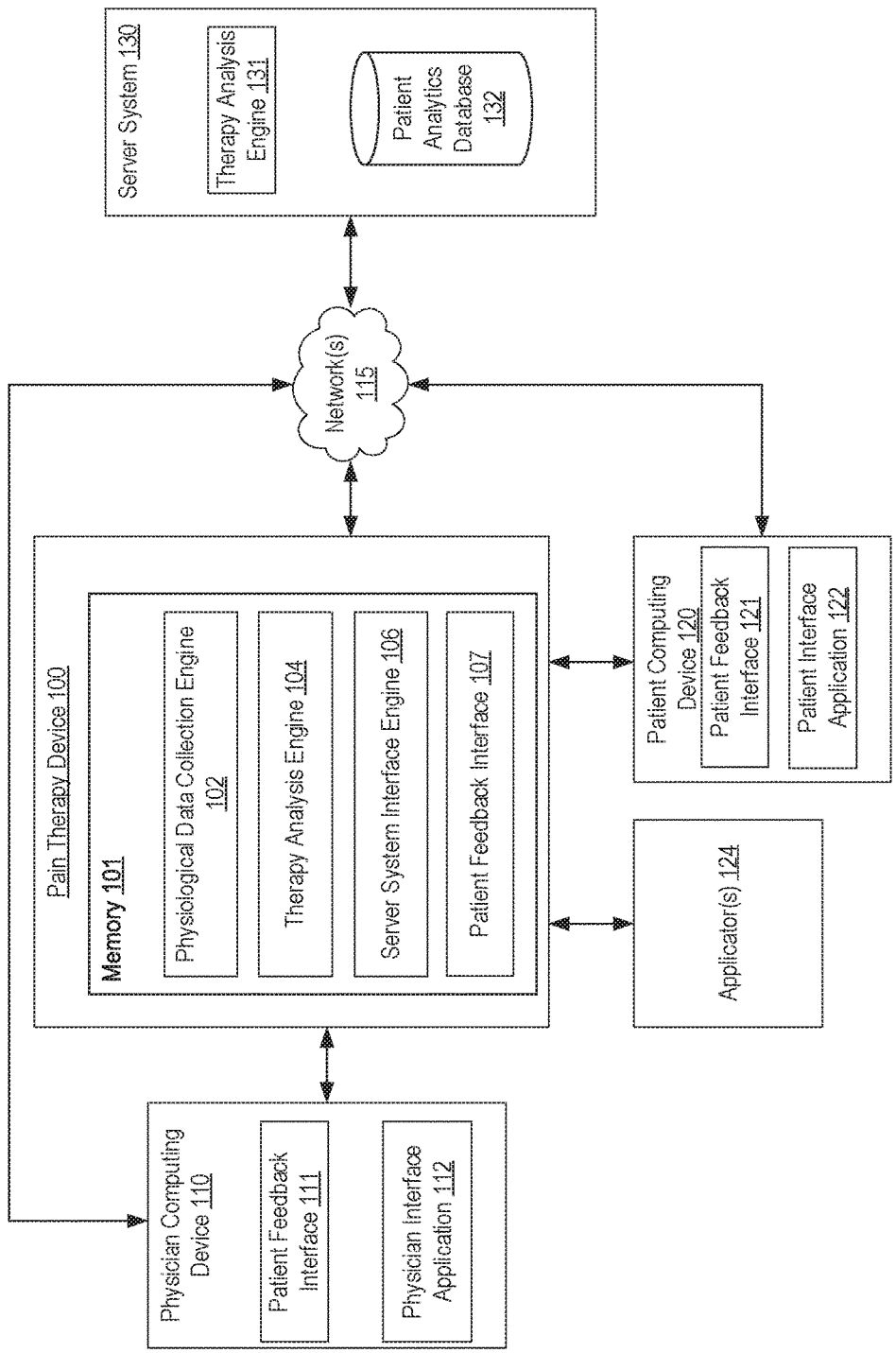
FIG. 1 is a block diagram depicting a pain therapy device communicating with a server system to provide personalized pain therapy that is adjusted based on subjective and objective feedback in response to the applied pain therapy.

Systems and methods are disclosed for pain management therapies and devices. System and methods are also disclosed for computer-implemented pain management through the use of a pain management device that applies a combination of physical therapies to alleviate pain symptoms and adjusts the application of the physical therapies based on feedback information. Feedback information includes physiological responses resulting from the applied therapy, patient feedback received as a pain relief score (e.g., a score from 0-10 or 0-5 as the case may be), and analytics information indicating the personalized pain management therapy for patients with similar demographics/pre-existing medical conditions and other characteristics as the current patient. The pain management therapy includes application of physical therapies via an applicator. Physical therapies include electroceuticals (i.e., any type electrical stimulation used for therapeutic benefit), thermoceuticals (e.g., defined as a "thermal therapy method or a device designed to affect biological systems and modify function(s) of the body to alleviate or mitigate symptomotology and/or pathology." As part of thermal therapy, thermal energy is delivered to the body or superficial or deep tissue using a variety of devices and methods known to those skilled in the art. The temperatures applied to the body locally or systemically and may vary from about −100° C. to +100° C.). Other possible pain management therapies include ultrasound. Any combination of these treatments may be combined, depending upon the patient and the condition to be treated. One exemplary device for managing pain is described in U.S. Patent Publication No. 2014/0200487, titled "Portable Electronic Therapy Device and the Method Thereof," which is incorporated by reference herein.

The physical therapies applied via the computer-implemented pain management therapy target specific physiological functions (i.e., without using any drugs) of the tissue through external non-invasive stimulation (or invasive stimulation) to provide pain relief. A variety of physiological functions can be influenced, simply by changing the temperature of the tissue (e.g., cold, or heat at superficial or deeper levels) using a variety of methods such as cold or hot packs/baths, infrared lamps, lasers, shortwave diathermy, microwave diathermy, therapeutic ultrasound, and radio frequency application. Some of the physiology induced changes include variations in cell membrane, or protein or nucleic acid structure and function, enzymatic activity, cell apoptosis, nerve conduction, coagulation, collagen fiber contraction, collagen synthesis, vasodilation, vasoconstriction, viscosity of body fluids/blood, cellular fluid crystallization or dehydration, pain signaling, production of endorphins, spasm, tissue metabolism, blood flow, inflammation, edema extensibility, supply of oxygen & nutrients, tissue/muscle repair or healing, fibroblast activity, collagen fibril density, protein synthesis, and tissue regeneration. Some of the physical medicine based therapeutic indications include pain (chronic or acute) relief, musculoskeletal pain relief, sports injuries, post surgical pain, post surgical edema, reduction in inflammation, reduction of joint contractures, fibromyalgia, migraine, tissue healing, swelling reduction, Hematoma resolution, acute bone healing, wound healing, face lift, wrinkle reduction, angiogenesis, removal of warts, cancer therapy, strains, contracture, decrease in muscle spasticity, tumors, capsulitis, bursitis, myositis, tendonitis, improving range of motion, rheumatoid arthritis and osteoarthritis.

Application of thermoceuticals includes both heat therapy and cold therapy. Heat therapy can ease pain by increasing blood flow to affected areas, which can help decrease inflammation, relax tight muscles and eliminate waste products such as lactic acid that cause stiffness and soreness. Likewise, application of cold may facilitate healing after injuries and limits musculoskeletal pain. Cold therapy induces a drop in skin temperature and a modest decline in temperatures within the muscles and joints, thereby causes arteriolar and capillary vasoconstriction in the skin leading to decrease in local synovial blood flow to reduce swelling. Thermoceuticals can be applied via any suitable mechanism for changing the temperature of the tissue. For example, thermoceuticals can be applied via surface heating/cooling using heat pack or cold packs or by microwave radiation, shortwave radiation, ultrasound application, infrared radiation.

Application of ultrasound therapies stimulates tissue beneath the skin's surface using sound waves at 1 or 3 MHz, depending on set parameter, the temperature rises up to 5° C. in 2-8 cm deep tissue. The ultrasound can also imparts non-thermal effects such as acoustic streaming and cavitation to provide pain relief. Thermal changes also result in activation of a wide variety of thermal receptors (transient receptor potential channels (TRP)) in the skin/tissue that range from 0-60° C., and may mask pain signals to the brain. Activation of these receptors either chemically (e.g., menthol activates TRPA1, TRPM8, while capsaicin activates TRPV1, TRPV3) or physically can lead to masking of the pain sensation. In some embodiments of the present disclosure, the pain signal to the brain is masked by providing a method/mechanism to maximize/overwhelm the signal(s) from an individual or multiple TRP channels located around painful musculoskeletal region. The distribution ratio of various temperature sensitive receptors in the body varies depending upon the body location. For example, upper part of the body comprises more heat temperature receptors than cold temperature receptors.

Embodiments disclosed herein also include computer-implemented pain therapy that applies electroceuticals as electrical stimulation of nerves. In electric stimulation, electrical current at distinct voltages, frequencies and intensities is delivered to the skin through electrodes (e.g., TENS, electric muscle stimulation, EMS, or neuromuscular electric stimulation, NMES). Pain is relieved by means of the pain gate mechanism involving activation of sensory fibers that mask the pain and/or suppressing of pain signals to the brain. Additionally, electrical stimulation can generate a physiological response to the irritation produced by electrical stimuli leads to the release of endorphins. Electrically pulsed stimulation also causes enhanced localized muscle activity and thereby increases blood circulation to remove metabolic toxins, thereby reducing pain symptoms.

The electroceuticals can be applied to the body using either low (2-20 Hz) or high frequencies (20-200 Hz) for treating pain and several other therapeutic indications. The voltages used for electric stimulation may vary from 10 V to 120V, while the wave forms applied could assume different shapes such as square, asymmetrical biphasic, and symmetrical biphasic. The stimulation could be applied to the body continuously or in pulsed mode or in burst mode to trigger different therapeutic mechanisms for treating ailments. Although, the therapeutic mechanism behind electric stimulation has not yet been unequivocally established, it is generally believed that electric stimulation enables the body to produce its own endorphins, increases local blood flow and mask pain signals via pain gate mechanism and several other hypotheses as proposed in the literature.

In some embodiments, the pain therapy device communicates with a physician computing device to provide personalized care via application of personalized pain management therapy through customized application of electroceuticals, and thermoceuticals. For example, a physician computing device can receive inputs from a healthcare provider for setting the initial physical therapy and adjusting the therapy as the treatment is applied. The initial pain management therapy may also be set via a patient computing device communicatively coupled to the pain therapy device. The initial pain management therapy indicates the specific combination and intensity levels of electroceuticals, thermoceuticals, and/or ultrasound. During treatment, sensors communicatively coupled to the pain management device detect the physiological responses resulting from the application of the pain management therapy. The pain therapy device also receives patient feedback indicating pain relief scores via a user interface for the patient computing device (or entered directly from the graphic user interface of pain therapy device). The pain therapy device continues to apply the physical therapies (e.g., the electroceuticals, thermoceuticals, ultrasound, acupuncture, pressure/massage based therapies) indicated in the therapy until the physiological responses/patient feedback indicates a threshold pain management level has been reached.

For example, as the pain management therapy is applied, the sensors coupled to the pain therapy device may detect an increase in blood flow or an increase in blood-oxygen levels at the localized area of pain. If the rate of blood flow and the value of the blood-oxygen levels reach a threshold value specified in the pain management treatment, the pain therapy device reduces or completes the application of the physical therapies. Similarly, the pain therapy device may receive feedback from the patient via a user interface indicating the pain has decreased (e.g., by indicating a pain relief score on a 0-5 or a 0-10 scale). In response, the pain therapy device continues or completes or modifies the application of the physical therapies. For example, a therapy analysis engine executing on the pain therapy device receives updates from a physiological data collection engine and from a patient feedback interface and uses the collected information to iterate the dosage of the physical medicine.

Embodiments disclosed herein also recognize that the demographics of chronic pain patients and the physical therapy requirements are unique. It has been well documented in the literature that people with certain pain symptoms, do not respond to electroceuticals and thermoceuticals (or even pharmaceuticals) in similar fashion. For example, some people may get pain relief using TENS, and others may not respond to such a therapy at all, and may even have allergic reaction. Therefore, the physiology of individuals and the patient feedback plays an extremely important role in determining the ideal/optimal therapy. In addition to being responsive to patient feedback and physiological response from an applied pain therapy, the pain therapy device further tailors or "titrates" physical medicine(s) dosage (energy type(s), intensity, exposure depth and duration) based on the patient demographics (e.g. age, gender, body mass index, ethnicity, pre-existing health conditions and cultural background). For example, the server system includes a patient analytics database that stores patient demographics and applied therapy information (e.g., the specific combination of the physical therapies applied and the dosage levels) as well as information on outcomes of the applied pain management therapy on multiple individuals that had previously applied pain management therapies. The database may comprise enormous amount of information from hundreds or thousands or even millions of individual patients and provides a powerful tool to conduct data analytics and customize the pain therapy for individuals either in an automated fashion or through prompt response from the physician. The analytics data can indicate the statistical likelihood of satisfactory pain management outcomes from application of the pain therapy.

The pain therapy device connects with the server system over a network to compare the patient information for a specific patient with the patient information in the analytics data to identify a subset of individuals that have similar characteristics as the patient. For example, the therapy analysis engine may comprise a software application or software module executing in either the pain therapy device or the server system. The therapy analysis engine identifies a subset of individuals that are with the same age range, gender, body mass index, and other pre-existing medical conditions, pain therapies received in the past or on-going (including drugs, or surgical procedures or alternate medicines), physical characteristics as the patient. The therapy analysis engine also identifies one or more pain management therapies that were applied to the subset of individuals that resulted in favorable pain management outcome. The pain therapy device can thus personalize the applied pain management therapy based on subjective data such as patient feedback, objective data such as physiological responses to the applied therapy, as well as analytics data that can indicate the personalized pain management therapy as collected from other patients with similar characteristics as the patient.

The pain therapy device can transfer the patient information and the pain management therapy information through wireless connectivity to the database for storage in the analytics system. In this way, the pain management adds the current patient's information (e.g., demographic information, symptoms, etc.), applied pain management therapy, and therapy outcomes (e.g., patient relief scores and physiological changes resulting from the therapy) to the analytics database.

These illustrative aspects and examples are given to introduce the reader to the general subject matter discussed here and are not intended to limit the scope of the disclosed concepts. The following sections describe various additional features and examples with reference to the drawings in which like numerals indicate like elements, and directional descriptions may be used to describe the illustrative aspects but, like the illustrative aspects, should not be used to limit the present disclosure.

FIG. 1 is a block diagram depicting a pain therapy device 100 that connects to a server system 130 over a network 115 to provide personalized pain management therapies based on measured physiological feedback data, subjective patient input data (e.g., a pain relief score), and analytics data compiled on other patients and applied pain therapies. The pain therapy device 100 can be communicatively coupled to a patient computing device 120 and/or a physician computing device 110 for receiving feedback to adjust the applied pain management therapy. The pain therapy device 100 includes a memory 101 that stores executable program code for performing operations described herein. For example, memory 101 includes program code for execution of a physiological data collection engine 102, a therapy analysis engine 104, a server system interface engine 106, and a patient feedback interface 107. In another embodiment, the server system 130 includes program code for the therapy analysis engine 131.

An initial pain management therapy may be programmed via physician computing device 110 or patient computing device 120. In some embodiments, the patient using the pain therapy device 100 may communicate directly with a health care provider via patient computing device 120 and physician computing device 110. The patient computing device 120 and the physician computing device 110 may comprise any suitable computing device, such as a personal computer, a tablet computer, or a cell phone. The initial pain management therapy may be personalized based on patient information (i.e. information on the user of pain therapy device 100). For example, the physician computing device 110 includes a physician interface application 112 that presents options for inputting patient information (e.g., patient pain symptoms, demographic information, medical history, and additional information) and a personalized pain management therapy based on the patient information. A healthcare provider operating the physician computing device 110 can prescribe the personalized pain management therapy via the physician interface application 112. For example, the physician interface application 112 presents a user interface for selecting a physical medicine via a combination of electroceuticals, or thermoceuticals. In other embodiments, the patient computing device 120 includes a patient interface application 122 for inputting patient information. Via the patient interface application 122, the patient provides inputs regarding the personalized pain management therapy as discussed or otherwise prescribed by the healthcare provider. The personalized pain management therapy can thus be administered via the health care provider or self-administered via the patient.

One or more applicators 124 connected to the pain therapy device 100 apply the personalized pain management therapy input via physician interface application 112 or patient interface application 122 or directly through physical therapy device 100. The personalized pain management therapy comprises of physical therapies that include a combination of electrical stimulation, hot and cold stimulation, and ultrasonic pulses. In some embodiments, based on feedback received from physician computing device 110 and patient computing device 120, the therapy analysis engine 104 executing on the pain therapy device 100 adjusts the applied personalized pain therapy accordingly. For example, inputs received via a patient feedback interface 111 presented on physician computing device 110 or patient feedback interface 121 presented on patient computing device 120 may indicate a pain relief score from a value of 0-10, with 10 indicating the most intense pain and 0 indicating no pain. It should be understood that other values or indications could be used, such as emoticons, descriptive text, color, or a selection on a continuum. As the personalized pain management therapy is applied via applicator 124, a pain relief score may be received indicating a low measurement of pain. A satisfactory application of personalized pain management therapy can be based, for example, on reduction of a pain relief score by a certain pre-programmed threshold. In response, the therapy analysis engine 104 may adjust the personalized pain management therapy by adjusting the dosages and intensities of physical therapies to accommodate for lesser pain. The feedback comprising the pain relief score may also be received directly on a user interface on pain therapy device 100. For example, memory 101 of patient therapy device 100 may include program code for executing a patient feedback interface 107 used to receive feedback to the therapy from the patient.

In further embodiments, the therapy analysis engine 104 adjusts the personalized pain therapy in response to physiological measurements detected via one or more sensors coupled to pain therapy device 100. For example, a physiological data collection engine 102 executing in memory 101 of pain therapy device 100 may receive information on the blood-oxygen levels, rate of blood flow, and tissue thickness from connected sensors. The personalized pain management therapy may include instructions on applying physical therapies at specific dosage levels and adjust the applied physical therapies in response to changes in physiological measurements. For example, the therapy analysis engine 104 may apply a combination of electrical stimulation at a certain intensity level, heat stimulation at a certain temperature, and ultrasonic pulses until a physiological responses indicate a blood flow of a certain rate. Once the specified blood flow rate (or blood oxygen levels) is achieved, pain therapy device 100 may apply physical therapies with different intensity levels/temperature values. This process continues until the pain management therapy is complete (e.g., the prescribed physical therapies are fully administered).

In additional embodiments, patient symptoms and demographic information on the patient (i.e. user of pain therapy device 100) may be compared with analytics information stored on multiple other patients to determine the personalized pain management therapy. The analytics data is stored on a patient analytics database 132 in server system 130 and comprises patient information compiled on numerous other patients. For example, the stored patient information includes data on prior patient demographics, prior patient pain symptoms, the pain management therapies previously applied on the other patients, and the outcomes of the pain management therapies (e.g., indicating satisfactory outcome, unsatisfactory outcome, etc.). The analytics data can also include the average pain feedback score that was indicated by the prior patients in response to previously applied pain management therapies.

In one embodiment, a server system interface engine 106 is a software application or module executing in pain therapy device 100. The server interface engine 106 transmits data comprising the patient information to server system 130. The server system interface engine 106 provides instructions for communicating the patient information to server system 130 and receiving information in response from server system 130. Based on the received patient information, a therapy analysis engine 131 executing on the server system 130 identifies a subset of individuals that have similar characteristics as the user of pain therapy device 100. For example, therapy analysis engine 131 may identify a subset of individuals that are in the same age range, have the same gender, have a similar body mass index as the user of pain therapy device 100, and/or have similar pain symptoms, or any combination thereof. The therapy analysis engine 131 may also identify a prior applied pain therapy among the subset of individuals that is associated with a pain therapy outcome indicating reduced pain symptoms. For example, the therapy analysis engine 131 may identify a prior applied pain therapy among the subset of individuals that indicates a satisfactory pain management outcome. A pain therapy with a satisfactory pain management outcome may include pain therapies that have resulted in reduced pain relief scores by a certain threshold (e.g., 2 points or more). A pain therapy with a satisfactory pain management outcome may also be indicated when a health care provider has approved a given therapy or removed a patient who has had a successful result with the therapy. A pain therapy with a satisfactory pain management outcome may also be indicated by accomplishment of objective physiological measurements such as reduction in inflammation or improvement in range of motion, improvement in local blood oxygen levels or flushing out toxins in the injured body part or visually observation of parameters such as wound healing or bone healing or any measurable parameters that either directly or indirectly correlate with reduction in pain as deemed appropriate by physician. The selected pain management therapy based on the analytics data is transmitted to the pain therapy device 100. Because the received pain management therapy is determined from prior therapies applied on patients with similar characteristics to user of pain therapy device 100, the received pain management therapy is personalized to the user of pain therapy device 100.

In another embodiment, the pain therapy device receives the analytics data on other patients from the server system 130. The therapy analysis engine 104 executing in pain therapy device 100 uses the received analytics data to select the subset of individuals that have similar characteristics as the user of pain therapy device 100. In this embodiment, the therapy analysis engine 104 identifies a personalized pain management therapy that, from the analytics data, indicates prior satisfactory outcome (e.g., reduction in pain symptoms).

The analytics data is depicted as stored in patient analytics database 132 in server system 130 for illustrative purposes. In other embodiments pain therapy device 100 stores the analytics data.

Figure 2:
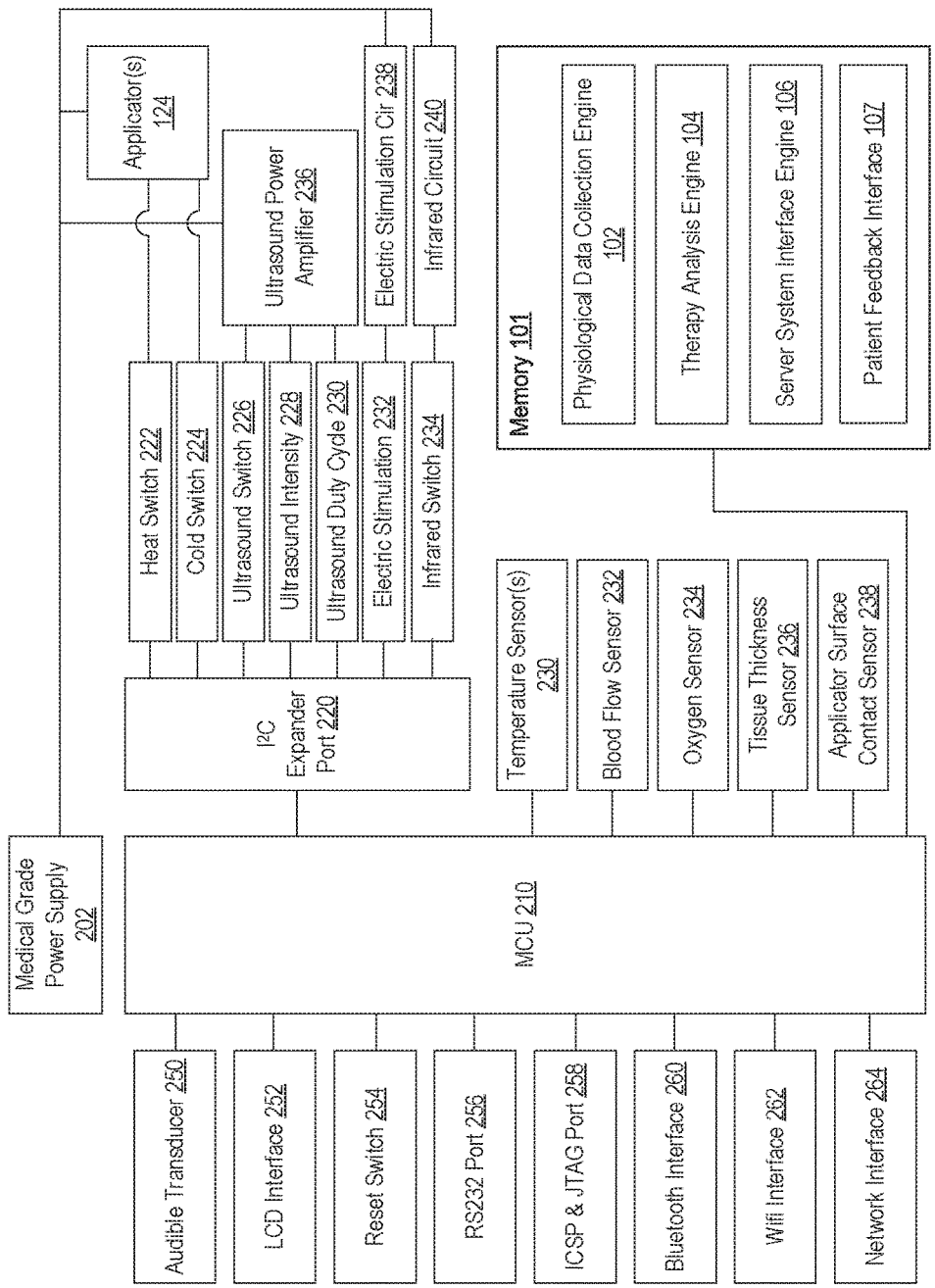
FIG. 2 is a block diagram illustrating the logical components of the pain therapy device shown in FIG. 1.

FIG. 2 depicts a block diagram illustrating the logical components of pain therapy device 100. Pain therapy device 100 includes a micro-controller unit (MCU) 210. MCU 210 includes processing devices such as an application specific integrated circuit (ASIC), or any general-purpose processor. MCU 210 can include logic for connecting to external interfaces 250-264. For example, MCU 210 includes an audible transducer 250, an LCD interface 252 (or interface for any other type of user interface device), a reset switch 254, an RS232 port 256, an Inter Circuit Serial Programming (ICSP) and Joint Test Action Group (JTAG) port 258, a Bluetooth interface 260, a WiFi interface 262, and a network interface 264 (e.g., an Ethernet port). The MCU 210 is also coupled to sensors for receiving physiological measurements from the user of pain therapy device 100. Said sensors include temperature sensor 230 (for measuring the body temperature of the patient at the point of contact of the applicator 124, blood flow sensor 232 (for measuring the blood flow rate at the point of contact of the applicator 124), oxygen sensor 234 (for measuring the blood-oxygen level at the point of contact of the applicator 124), tissue thickness sensor 236 (for measuring the thickness of the tissue at point of contact of applicator 124), and an applicator surface contact sensor 238 (for detecting if the applicator 124 is in contact with tissue. In some embodiments, sensors 230-238 can be included as part of applicator 124 (as shown further below in FIG. 3).

The MCU can also include or be in communication with a computer-readable medium storing instructions that, when executed by the MCU 210, cause the MCU 210 to perform the operations described herein. For example, the MCU 210 is in communication with memory 101, which includes any suitable non-transitory computer-readable medium. The computer-readable medium includes any electronic, optical, magnetic, or other storage device capable of providing a processor with computer-readable instructions or other program code. Non-limiting examples of a computer-readable medium include a magnetic disk, memory chip, ROM, RAM, an ASIC, a configured processor, optical storage, magnetic tape or other magnetic storage, or any other medium from which a computer processor can read instructions. The instructions include processor-specific instructions generated by a compiler and/or an interpreter from program code written in any suitable computer-programming language, including, for example, C, C++, C#, Visual Basic, Java, Python, Perl, JavaScript, and ActionScript. The program code includes one or more of a physiological data collection engine 102, therapy analysis engine 104, server system interface engine 106, and patient feedback interface 107.

The MCU 210 can also be communicatively coupled to control inputs 222-234 for controlling the characteristics of the pain management therapy as applied by applicator 124. Control inputs 222-234 include a heat switch 222, cold switch 224, ultrasound switch 226, ultrasound intensity control 228, ultrasound duty cycle 230, electric stimulation switch 232, and infrared switch 234. Ultrasound switch 226, ultrasound intensity control 228, and ultrasound duty cycle control 230 (which control the respective characteristics of the ultrasound pulses that are part of the pain management therapy) are fed to ultrasound power amplifier 236. Ultrasound power amplifier 236 provides necessary amplification of the signals before driving the ultrasound output of applicator 124. The output from electric stimulation switch 232 can be fed to electric stimulation circuit 238 before driving the electrical characteristics of applicator 124. Similarly, output from infrared switch 234 can be fed to infrared circuit 240 before driving infrared output of applicator 124. Via heat switch 222 and cold switch 224, temperature characteristics of applicator 124 can be specified. The output of heat switch 222 and cold switch 224 for controlling the temperature characteristics are provided to applicator 124. In some embodiments, the control inputs 222-234 can be coupled to MCU 210 via an I$^2$C expander port 220.

A medical grade power supply 202 can provide the power requirements to the components herein. For example, medical grade power supply 202 provides power to ultrasound power amplifier 236, applicator 124, electric stimulation circuit 238, and infrared circuit 240.

Figure 3:
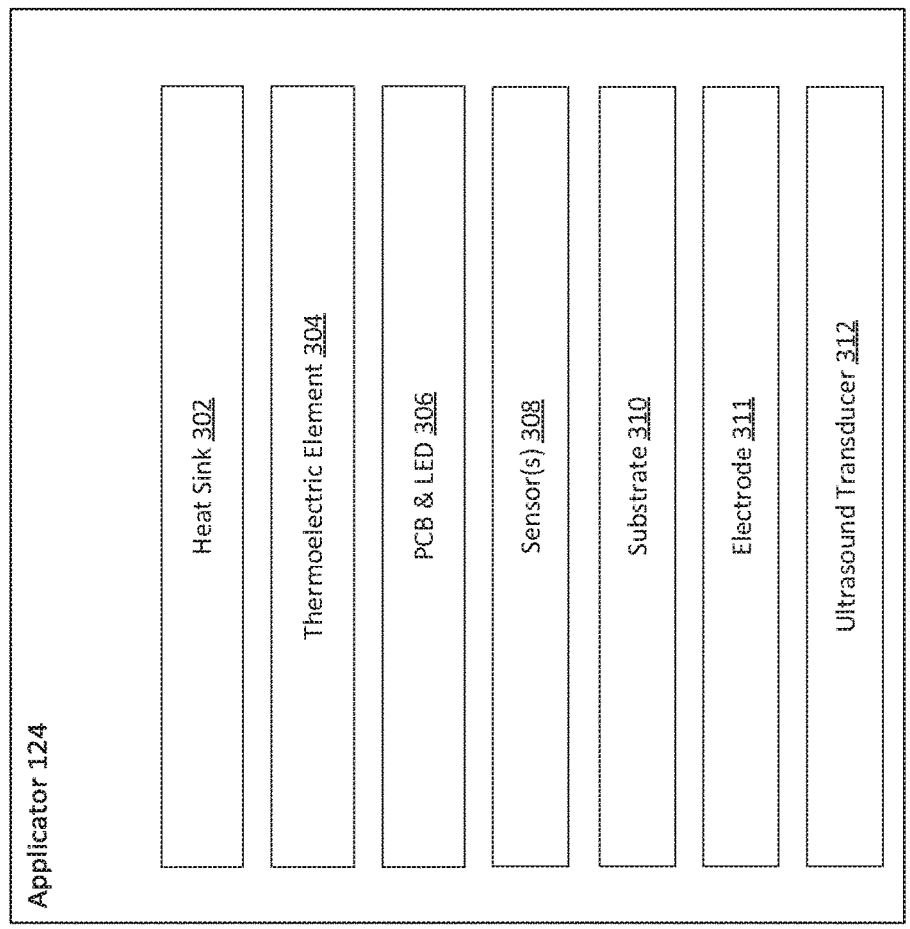
FIG. 3 is a block diagram depicting the various components present in the applicator for applying the pain management therapy.

FIG. 3 illustrates a representation of the various components present in the applicator 124, as shown as different layers. The sequencing of the various layers could be altered and does not necessarily have to be in the order shown in FIG. 2. Further, multiple layers/components of the applicator 124 could be embedded into a single layer or form physically distinct layers. The control inputs 222-234 provide the electrical signals that control the various layers of applicator 124. The layers for applicator 124 can be placed on the surface area of the tissue of the patient for whom the pain management therapy is applied.

Applicator 124 can include a heat sink component 302, which measures the temperature of the tissue on which the applicator 124 is applied. The thermoelectric element component 304 applies the hot or cold temperature as specified by heat switch 222, cold switch 224, and the specific temperature as set by MCU 210. The applicator 124 can also include a PCB & LED component 306 that can display. The PCB inside the applicator integrates the thermoelectric elements, sensors, ultrasonic transducer and TENS electrodes and simplifies the connectivity. The PCB is also capable of connecting to any additional sensors or thermal energy generating transducers integrated into the applicator (e.g., blood flow detection sensor, infra-red radiation source etc.). The LED component visually indicates the status of applicator such as ON or OFF (especially, for the convenience of care providers). In some embodiments, the applicator 124 can also include built in sensors 308, which include one or more of the temperature sensor 230, blood flow sensor 232, oxygen sensor 234, tissue thickness sensor 236, and applicator surface contact sensor 238. Applicator 124 can also include a substrate component 310 and/or electrode component 311 for applying the electrical impulses as driven by electric stimulation circuit 238. Applicator 124 can also include an ultrasound transducer for applying the ultrasound impulses driven by ultrasound power amplifier 236.

In some embodiments, the sensors 308 measure the substrate 310 and/or electrode 311 temperature and send the temperature to the MCU 210. The ultrasound transducer 312 can be utilized by the therapy analysis engine 104 to identify the thickness or depth of the tissue based on ultrasound reflection intensity measured. This kind of sensing feature helps provide for the inclusion of safety features regarding the device usage on different parts of the body (e.g., it is possible to prevent the usage of the device on the head or skull of the patient). The sensing feature also enables the determination of physical dosage to be delivered to a targeted area.

Figure 4:
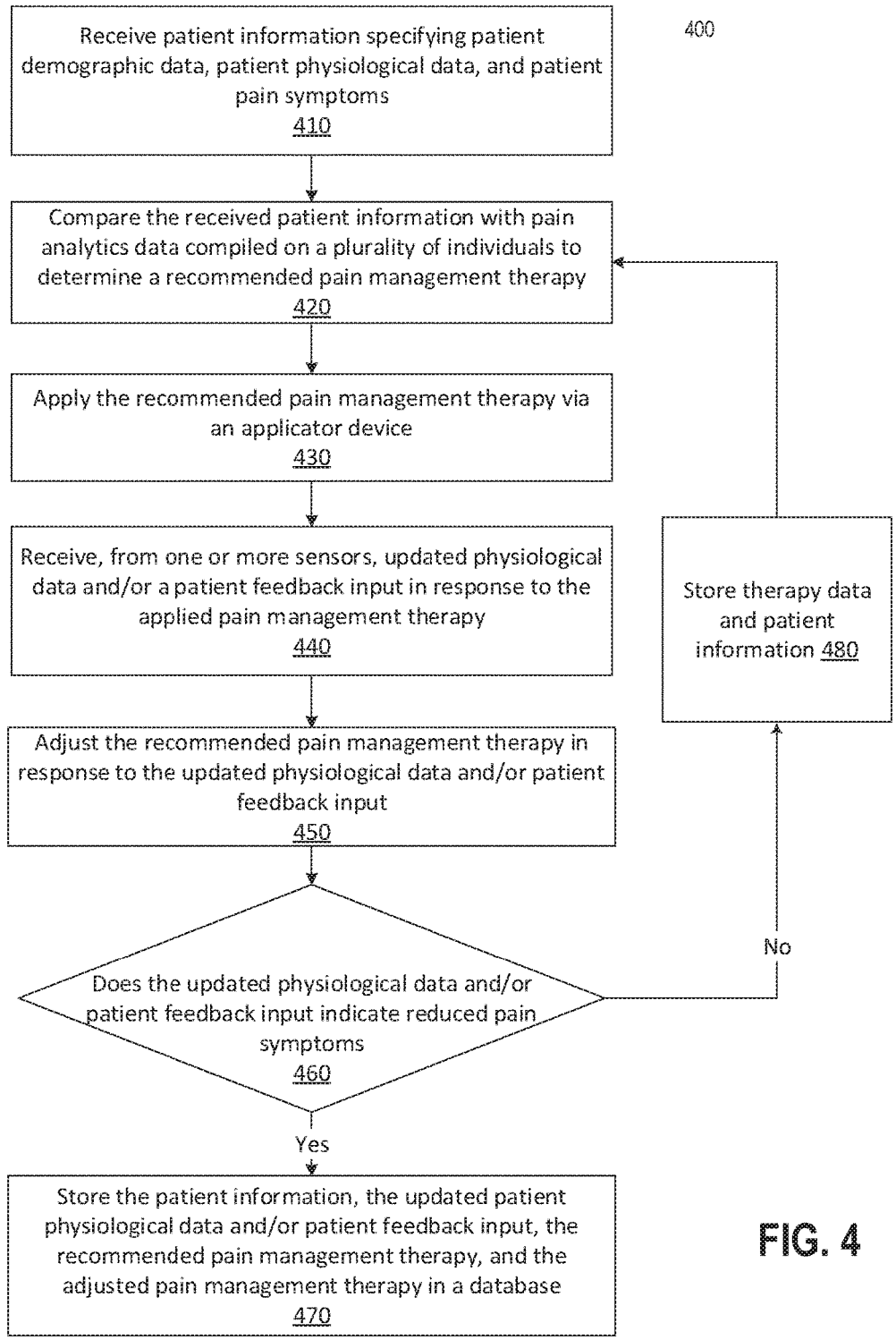
FIG. 4 is an flowchart depicting an example process for applying a personalized pain management therapy based on stored analytics data and adjusting the applied therapy based on feedback.

FIG. 4 is a flowchart depicting an example process 400 for applying a personalized pain management therapy based on stored analytics data on numerous other prior patients and adjusting the applied therapy based on physiological feedback. The process 400 may be performed by one or more of the components listed in FIGS. 1-3 or in any suitable computing and/or communication environment.

The process 400 involves receiving patient information specifying patient demographic data, patient physiological data, and patient pain symptoms, as shown in block 410. Demographic data can include information on patient such as age, gender, body weight and BMI, race, and geographic information. Patient pain symptoms include descriptions of patient pain symptoms and indications of pain. For example, patient pain symptoms can include a graphical indication of a body part (e.g., by selection of an area of a body on a touch screen) to show areas of localized pan, textual descriptions of the areas of localized pain, and a numeric pain relief score indicating the severity of the pain at the specified location. Pain symptoms can also be more or less detailed. All common chronic pains and musculoskeletal pains such as back pain, neck pain, shoulder pain, arthritis, muscle spasms, tendonitis, bursitis, sports injuries are either visually or verbally represented. Any other form of pain that requires diagnosis by qualified physician (e.g., fibromyalgia) or that cannot be treated using pain therapy device (visceral pain, especially involving cutting, burning and/or involving internal organ damage) will not be included in the system as a default. Patient physiological data includes physiological measurements of a measured tissue area. Physiological measurements include, for example, the measured rate of blood flow, blood-oxygen levels, tissue depth, tissue temperature, and other measurements. The patient information may be received via inputs in physician interface application 112 in physician computing device 110 or patient interface application 122 in patient computing device 120 and transmitted to pain therapy device 100. In other embodiments, the patient information can be directly entered in pain therapy device 100 via a user interface on the pain therapy device 100. While the pain therapy device 100 can process the patient information to determine the personalized pain management therapy, in other embodiments, the patient information is transmitted to server system 130.

Process 400 also includes comparing the received patient information with pain analytics data compiled on a plurality of individuals to determine a recommended pain management therapy, as shown in block 420. For example, the server system 130 includes a patient analytics database 132 that stores the pain analytics data on numerous prior patients. The pain therapy device 100 can transmit the patient information to the server system 130 for the comparison. In other embodiments, the pain therapy device 100 can receive the analytics data from the server system 130 via network 115 for the comparison.

Therapy analysis engine 104 (executing in pain therapy device 100) or therapy analysis engine 131 (executing in server system 130) compares patient information with the pain analytics data to determine a subset of individuals with similar characteristics as the patient as explained above with respect to FIG. 1. Additionally, therapy analysis engine 104 or therapy analysis engine 131 identifies the recommended pain management therapy that previously depicted a satisfactory outcome (e.g., by lower received pain relief scores from other patients, from objective measurements of physiological data indicating lesser pain symptoms).

As shown in block 430, the recommended pain management therapy is applied via an applicator device 124. For example, the applicator device 124 provides one or more electroceuticals, or thermoceuticals, or ultrasound, or any combination at a specific frequency, intensity, and/or duration as specified by the recommended pain management therapy. Note in some aspects, the recommended pain management therapy can be overridden and manually input via inputs received from physician computing device 110 or patient computing device 120.

After application of the recommended pain management therapy (which is initially based on the analytics data on pain management therapies applied on other patients), the pain therapy device 100 can further adjust and personalize the therapy based on feedback from the patient. As shown in block 440, process 400 further involves receiving, from one or more sensors, updated physiological data reflecting changes in the patient physiological data, and subjective patient feedback (in the form of pain score) in response to the applied recommended pain management therapy. For example, as the recommended pain management therapy is applied by applicator 124, sensors 230-238 measure changes in the temperature, blood flow rate, blood-oxygen levels, and tissue thickness resulting from the therapy. The sensor data can be received via a physiological data collection engine 102. The changes in the physiological data in response to the applied pain management therapy can be considered objective feedback to the pain management therapy.

Note that while the type of feedback in response to the applied pain management therapy described in block 440 is feedback from physiological data, other types of feedback are also possible. For example, the pain therapy device 100 can receive subjective feedback from the patient in the form of a patient relief score (e.g., a numeric value from 0-10) as discussed above with respect to FIG. 1.

The therapy analysis engine 104 can adjust the applied pain management therapy in response to the changes in physiological data (or in response to other feedback), as shown in block 450. For example, the applied voltage or current of the electrical stimulation, the temperature of the heating element, or the intensity of the ultrasonic pulses can be adjusted based on the changes in the physiological data or based on patient feedback. Probably, the pain relief scores from patients in conjunction with objective physiological data (whenever available) could be used to adjust or titrate the dosage of the physical medicine involving single or combination of therapies. For example, the thermoceutical dosage may be defined by three parameters, i.e., intensity (e.g., temperature range; frequency, intensity and duty cycle in case of ultrasound), energy exposure time, and course duration for a given tissue thickness or composition (or BMI). If the physical medicine dosage delivered does not increase the tissue temperature or raise the deep tissue temperature in stipulated time frame and/or for sustained time period, and/or do not provide pain relief to the patient, one could consider the dosage delivered is sub optimal. At present, our understanding about how distinct physical modalities or their combination therapies at what dosage levels provide efficient pain relief is relatively limited. Further complexity stems from the fact that pain is a subjective personal experience, and the physiology of individual is different from each other and the way each individual responds to given therapy is unknown. If a patient does not respond to a particular electroceutical or thermoceutical pain therapy, it is not generally implied that the given therapy does not work; it only implies that given therapy is not appropriate for that patient. Therefore, it is important to identify the patterns from various therapies provided to patients with diverse backgrounds and profiles to develop a personalized pain therapy. Typically, the dosage delivered will always be within the safety limitations as outlined by data published in the literature, the dosages will be titrated based on positive response from patients (i.e., lower pain scores). Once adequate data is accumulated from patient responses, it is possible to correlate pain relief measured in response to given physical medicine dosage with quantifiable physiological data or body reflex related measurements (e.g., increase local blood flow of injured body part, thermal imaging, tissue temperatures, blood oxygen levels, sensitivity to pressure etc.) and constitutes one of the inventive aspect of this innovation.

As shown in block 460, the therapy analysis engine 104 makes a determination as to whether the updated physiological data indicates reduced pain symptoms. For example, the physiological changes in treated body part may include vasodilation, vasoconstriction as quantified by blood flow volume or velocity or by variation in blood oxygen levels or simply by measurement of tissue temperature or measurement of pressure sensitivity to pain (using algometer) or it could even include identification/measurement of certain cellular or molecular changes or electrical signals caused in response to external stimulation.

If the updated physiological data or patient feedback indicates reduced pain symptoms (it is possible that subjective and objective evaluation results may not converge, the patient feedback coupled with statistics may precede physiological measurements), the patient information, patient feedback, the updated physiological data, the recommended pain management therapy, and the adjusted pain management therapy are stored in the analytics database, as shown in block 470. For example, physiological data indicating reduced pain symptoms can be considered a satisfactory application of the pain management therapy. To add to the pain analytics database, the server system interface engine 106 executing on pain therapy device 100 can transmit one or more of the patient information (indicating the initial set of physiological measurements), the updated physiological measurements, the recommended pain management therapy (as derived from the pain analytics database), and/or the adjusted pain management therapy (as adjusted based on this individual patient's physiological responses) to the server system 130. The server system 130 stores the received information in patient analytics database 132.

If the updated physiological data and/or patient feedback does not indicate reduced pain symptoms, a different pain management therapy may need to be selected. In response to the lack of reduction of pain symptoms, the patient information, updated physiological measurements, recommended pain management therapy, and adjusted pain management therapy are first stored in the analytics database, as shown in block 480. This adds to the database and indicates a therapy that does not necessarily work for patients with characteristics similar to the user of pain therapy device 100. The process 400 then returns to block 420, where the therapy analysis engine 104 compares the patient information with pain analytics data to determine a different pain management therapy. The process 400 continues until a satisfactory pain management therapy is found.

Figure 6:
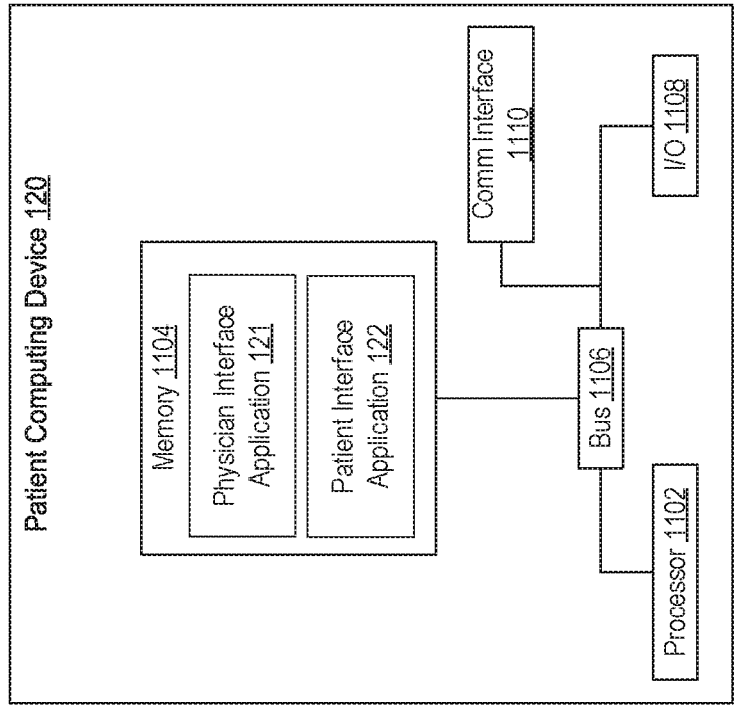
FIGS. 5 and 6 are block diagrams depicting example hardware implementations for some of the components shown in FIG. 1.

Any suitable computing system or group of computing systems can be used to implement the physician computing device 110 and the patient computing device 120 described in FIG. 1. For example, FIGS. 5-6 are block diagrams depicting examples of implementations of such components.

Figure 5:
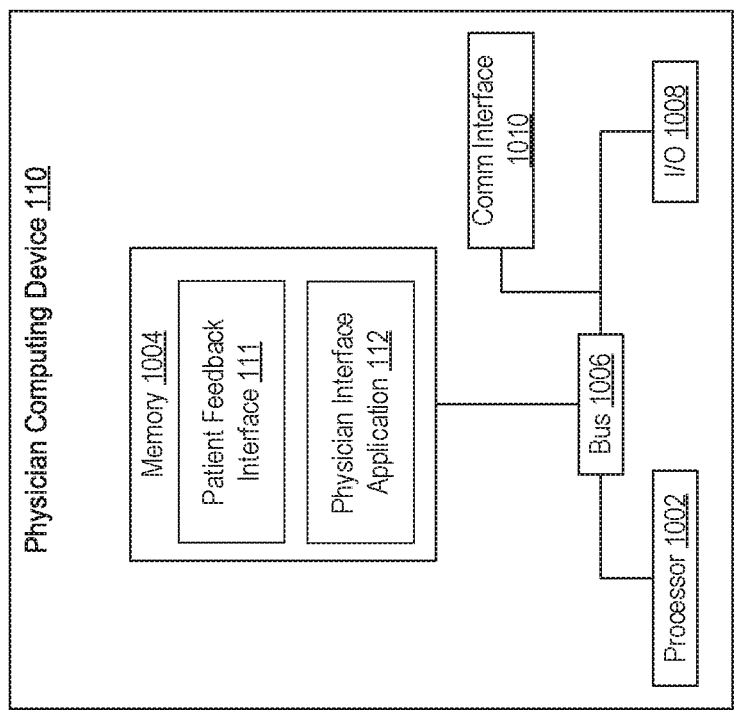

As shown in FIG. 5, the physician computing device 110 includes a processor 1002 that is communicatively coupled to a memory 1004 and that executes computer-executable program code and/or accesses information stored in the memory 1004. The processor 1002 comprises, for example, a microprocessor, an application-specific integrated circuit ("ASIC"), a state machine, or other processing device. The processor 1002 includes one processing device or more than one processing device. Such a processor is included or may be in communication with a computer-readable medium storing instructions that, when executed by the processor 1002, cause the processor to perform the operations described herein.

The memory 1004 includes any suitable non-transitory computer-readable medium. The computer-readable medium includes any electronic, optical, magnetic, or other storage device capable of providing a processor with computer-readable instructions or other program code. Non-limiting examples of a computer-readable medium include a magnetic disk, memory chip, ROM, RAM, an ASIC, a configured processor, optical storage, magnetic tape or other magnetic storage, or any other medium from which a computer processor can read instructions. The instructions include processor-specific instructions generated by a compiler and/or an interpreter from code written in any suitable computer-programming language, including, for example, C, C++, C#, Visual Basic, Java, Python, Perl, JavaScript, and ActionScript.

The physician computing device 110 also comprises a number of external or internal devices such as input or output devices. For example, the physician computing device 110 is shown with an input/output ("I/O") interface 1008 that receives input from input devices or provide output to output devices. A bus 1006 is also included in the physician computing device 110. The bus 1006 communicatively couples one or more components of the physician computing device 110.

The physician computing device 110 executes program code that configures the processor 1002 to perform one or more of the operations described above. The program code includes one or more of the patient feedback interface 111 or the physician interface application 112. The program code is resident in the memory 1004 or any suitable computer-readable medium and is executed by the processor 1002 or any other suitable processor. In additional or alternative embodiments, one or more modules are resident in a memory that is accessible via a data network, such as a memory accessible to a cloud service.

The physician computing device 110 also includes a communication interface 1010. The communication interface 1010 includes any device or group of devices suitable for establishing a wired or wireless data connection to one or more data networks 115. Non-limiting examples of the communication interface 1010 include an Ethernet network adapter, a modem, and/or the like. The physician computing device 110 transmits messages as electronic or optical signals via the communication interface 1010.

Similar to the physician computing device 110, the patient computing device 120 also includes a processor 1102, I/O interface 1108, communication interface 1110, and memory 1104 communicatively coupled via a bus 1106. The memory 1104 includes non-transitory computer-readable memory as described above and stores program code defining operations of the patient computing device 120. The processor 1102 executes the computer-executable program code and/or accesses information stored in the memory 1104. For example, the patient computing device 120 includes memory 1104 that stores program code for the physician interface application 121 and the patient interface application 122.

The following paragraphs describe further illustrative embodiments for the pain therapy device 100.

There may be provided a pain therapy device that is useful in treating various physiological conditions. The device may include a controller, sensors and an applicator. The applicator generally features a plurality of transducers that produce electrical, heat, cold and ultrasound energies respectively. The controller provides the required electronics to control energies produced by the transducers. The controller is configured to modify the intensity, timing, or duration of the different energies, which are applied over the treatment area (skin) over the feedback control signal obtained from the sensors. Both the controller and the applicator may be cooperate either by wired communication or can communicate wirelessly. They may be integrated into a single product.

The pain therapy for use herein can carry out therapeutic treatment using the lowest possible energy intensities in order to achieve a therapeutic effect. One or more of a combination of electric stimulation (electroceuticals), thermal stimulation (thermoceuticals via application of heat, cold) or ultrasound (pulsed or continuous), when applied to the treatment area in a systematic manner, has been demonstrated to show synergistic effect leading to better and faster therapeutic relief.

Superficially applied heat follows a top-down heating mechanism through conduction and heat may not get transferred beyond top 1 cm to 2 cm depth of the tissue (note that skin and tissue beneath it are poor thermal conductors). On the other hand, ultrasonic energy can heat up both surface and deep tissue (from 1 cm to 5 cm) easily as the acoustic energy absorbed by the tissue gets converted into thermal energy. Because of these fundamentally distinct modes of heating (conductive heating vs. converted heating), use of ultrasound and superficial heat combination rapidly creates a thermal gradient across the treated tissue leading to significantly higher blood flow rates quickly unlike conventional single form of thermal energy based therapies. Therefore, it is possible to provide improved oxygen supply to injured body part for sustained periods of time, and flush out unwanted inflammation causing chemicals to provide rapid and sustained pain relief.

Cold also follows a top-down thermal conduction, where cooling of the dermal and sub-dermal layers (top 1 cm to 2 cm) shows several beneficial effects with regard to treating acute injuries. Cold can decrease cellular metabolism and causes vasoconstriction of the blood vessels in the area and decreases the inflammation in the area and thus the associated pain and swelling. In combination with ultrasound, cold may provide an additive effect. For example, combination of cold and ultrasound energies together can create an inverse thermal gradient for improved blood flow, that is, the surface temperatures of the top most tissue layer will be below body temperature, while the deep tissue temperatures will be above body temperature. Indeed, such an inverse thermal gradient which is practically impossible to accomplish from conventional thermal therapies may be extremely useful for safely heating deep tissue to 45-70° C. rapidly for shorter time periods for face lifting and cosmetic applications.

Providing these energies in a controlled pulsatile manner can help reduce the risk of adverse effects, while still achieving the desired therapeutic effect.

Because a larger volume of dermal and sub-dermal tissues can be exposed to the energies when used in combination, especially thermal energy and ultrasound, there may be increased blood flow around the treatment area providing fresh oxygen and nutrients, and increasing subsequent tissue metabolism. Similarly, the combination of electric stimulation (e.g., TENS) and thermal stimulation may offer synergetic benefits both in terms of improving local blood flow and efficiently masking pain signals. Therefore, combination therapies not only account for individual patient related physiologies, but also provide an opportunity to precisely fine tune or titrate body reflexes across the deep tissue to provide rapid pain relief and other related therapeutic benefits (e.g., faster tissue regeneration giving relief from pain, wound healing, blocking pain sensation reducing pain, inflammation, spasms, and other side effects).

In one example, pulsed heating may be synchronized with pulses of pressure waves such that both pulses reach the target simultaneously. In another example, pulsed cooling may be synchronized with pulses of pressure waves such that both pulses reach the target simultaneously. In another example, pulsed heating is followed by pulsed cooling and both are synchronized with pulses of pressure waves such that both pulses reach the target simultaneously. In another example, TENS, ultrasound and surface heating can be synergistically applied to treat the entire cross section of the tissue. In another example, TENS, ultrasound and cold could be synergistically applied to accomplish targeted goals. The recent scientific advances made in medicine us realize that personalizing the medication or therapies is critical for achieving efficacious therapeutic benefits across the diverse population. The current approaches of using physical medicine indiscriminately across the various patient population leads to application of inconsistent therapies, and dosages and results in inefficient or inferior therapies, which may be randomly successful or unsuccessful. For example, the tissue thickness of a 300 pound person is different from 100 pound person, and so is the composition of the tissue, but if one applies electroceuticals or thermoceuticals identically to both these weight groups, the results may not be identical—after all, the applied energies are identical, but not the injured body parts. Further, the pathophysiology of each individual is different, and it is difficult to provide universal medicine for pain without personalizing it, especially physical medicines that do not cause adverse side effects. One more complex problem associated with pain is that patients' opinions/perceptions regarding pain are subjective and cannot be measured independently/objectively. Patients perceptions about pain (especially chronic pain) may dynamically change, their response to a particular therapy may also change either positively or negatively over a period of time. Therefore, personalization of precisely dosed combination therapies accounting patient feedback provides an unprecedented opportunity to treat pain safely and efficiently.

Figure 7:
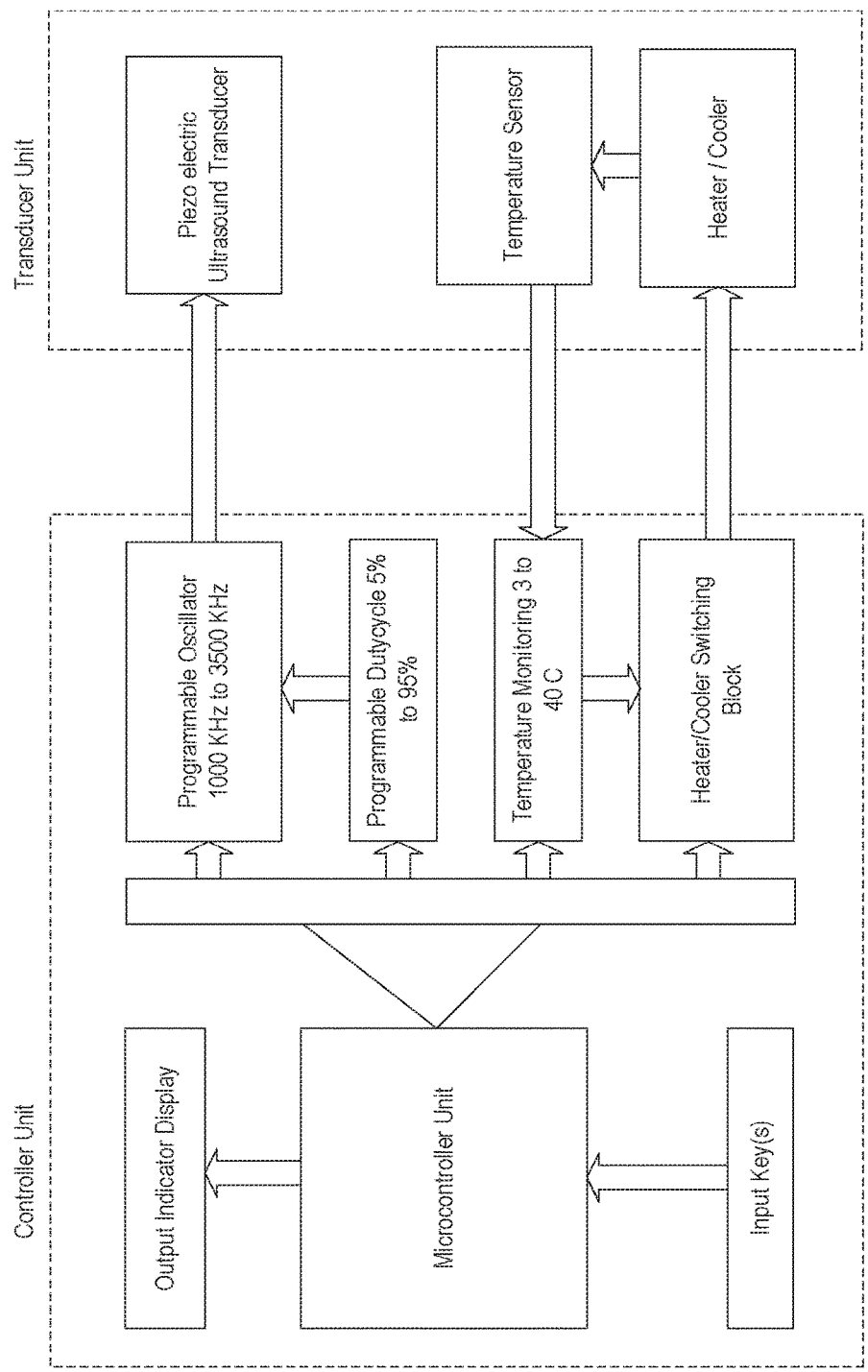
FIG. 7 is a block diagram depicting one example of a pain therapy device.

FIG. 7 shows a schematic block diagram of an exemplary pain therapy device. This device may be used with the treatment methods described herein. The device includes a controller and applicator. The power is provided by a battery or capacitor of a suitable power supply unit. The controller includes a microprocessor unit and controls a plurality of electronic circuit modules for the generation of different energy, such as thermal energy (0 to 70° C.) and ultrasound (0.2 to 20 MHz). The controller may be programmed for the duration, switching sequence and intensity of each of these energies. The applicator may include transducers capable of delivering heat, cold and ultrasound to the skin/treatment area. The applicator also features a plurality of sensors for the purpose of feedback and control. The sequencing of the various layers could be altered and does not necessarily have to be in the order as shown in figures.

Figure 8A:
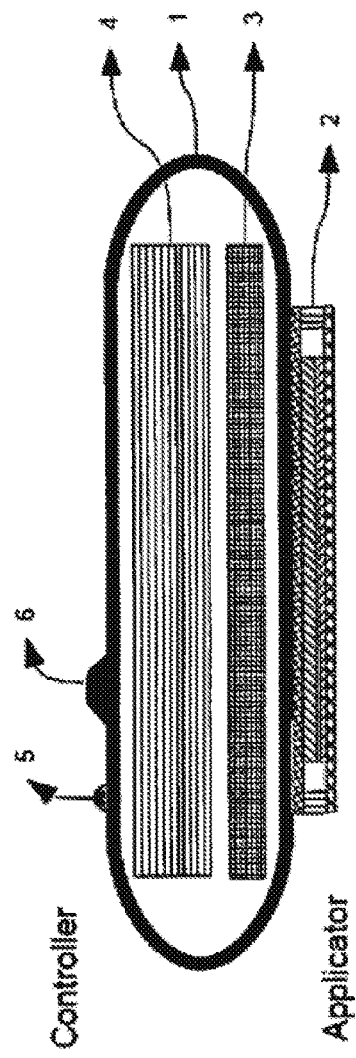
FIGS. 8A and 8B illustrate schematic cross sections of exemplary configurations of the pain therapy device.
Figure 8B:
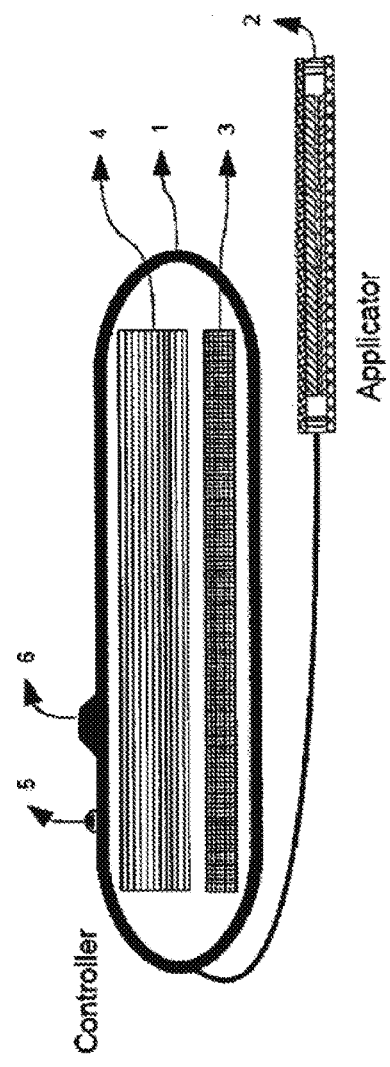
Figure 9A:
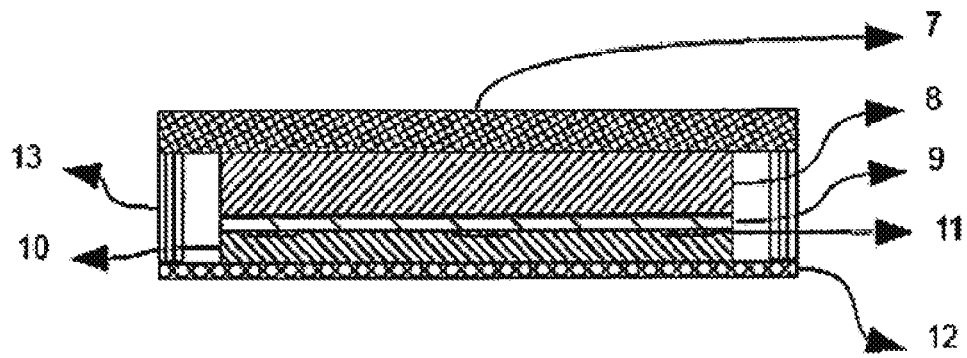
FIGS. 9A, 9B, and 9C illustrate schematic cross sections of exemplary applicator configurations and corresponding transducer arrangements.
Figure 9B:
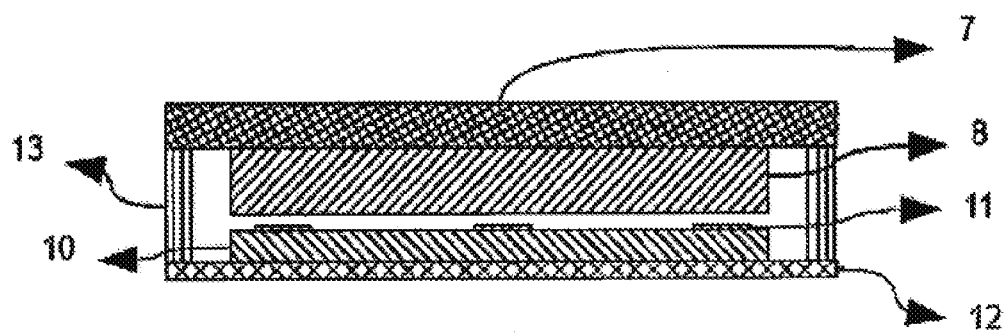
Figure 9C:
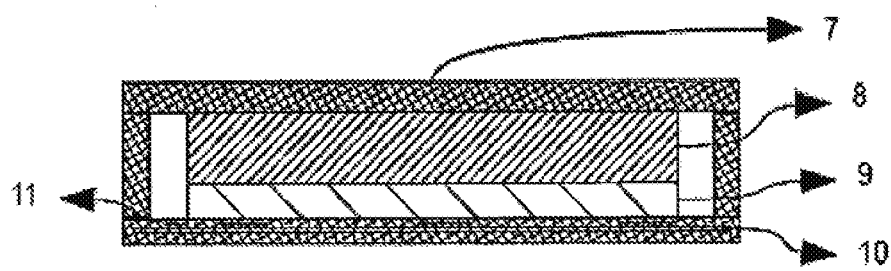
Figure 10A:
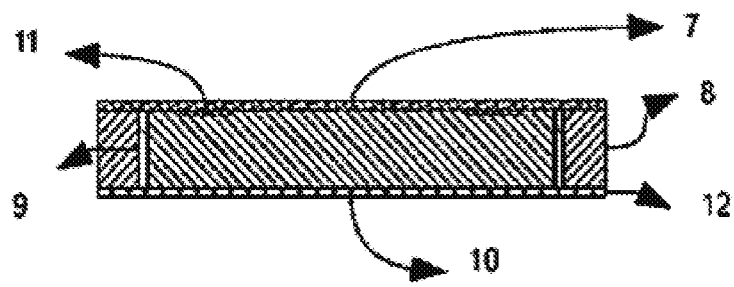
FIGS. 10A and 10B illustrate further schematic cross sections of exemplary applicator configurations and corresponding transducer arrangements.
Figure 10B:
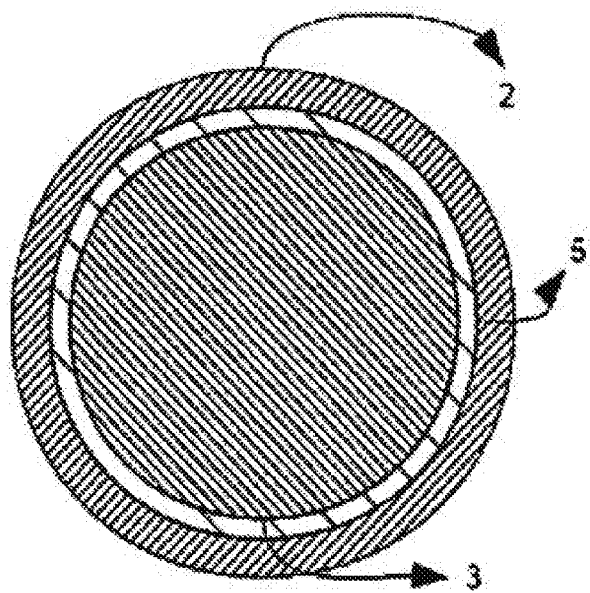
Figure 11A:
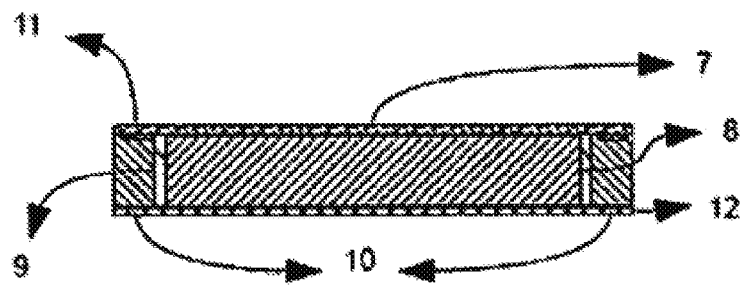
FIGS. 11A and 11B illustrate further schematic cross sections of exemplary applicator configurations and corresponding transducer arrangements.
Figure 11B:
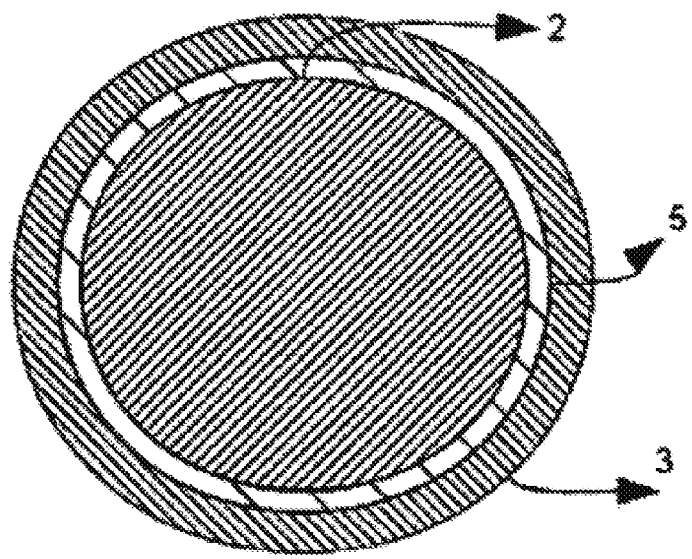
Figure 12A:
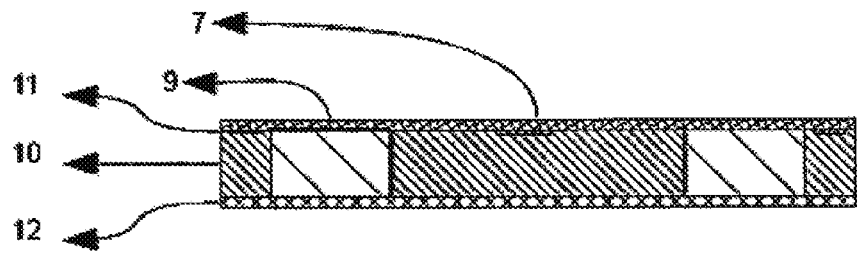
FIGS. 12A and 12B illustrate further schematic cross sections of exemplary applicator configurations and corresponding transducer arrangements.
Figure 12B:
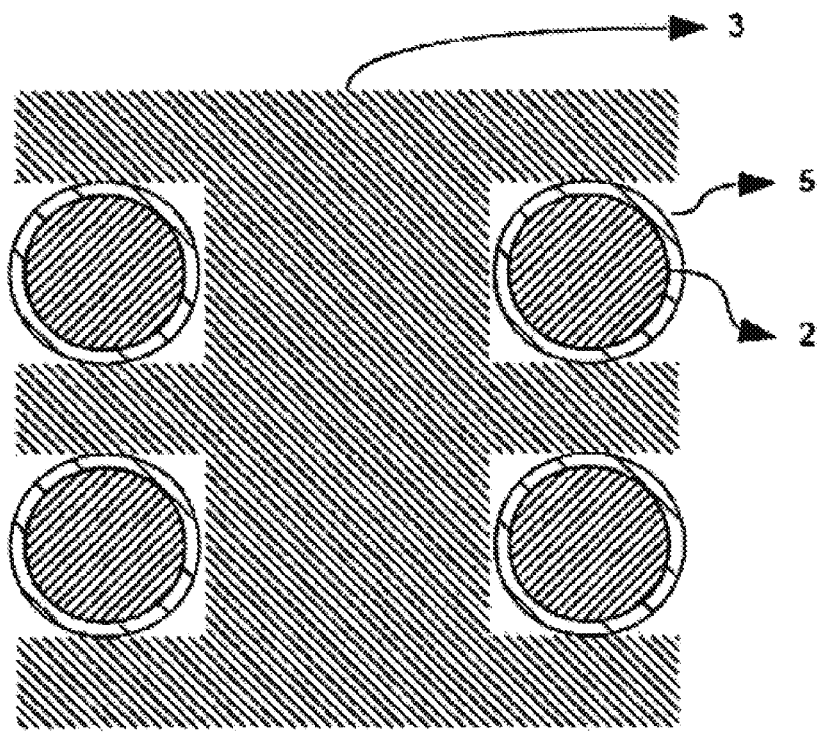
Figure 13A:
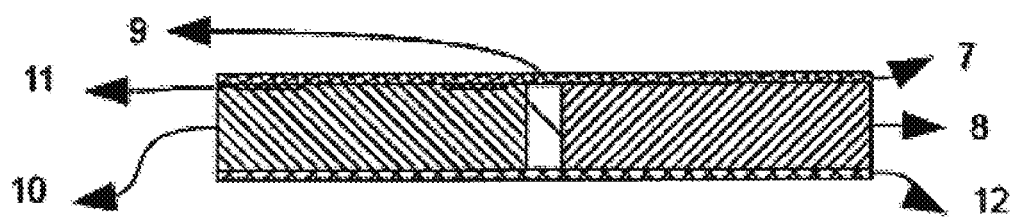
FIGS. 13A and 13B illustrate further schematic cross sections of exemplary applicator configurations and corresponding transducer arrangements.
Figure 13B:
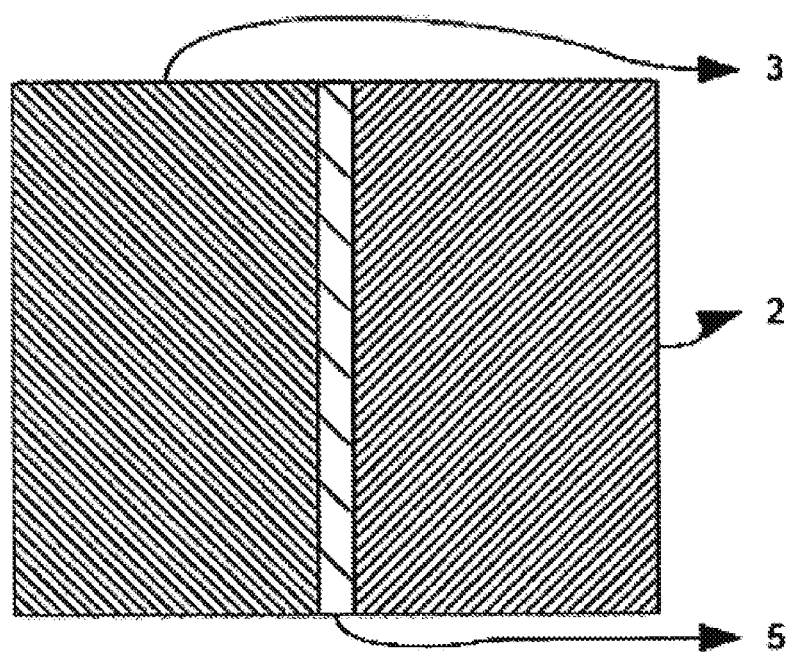

FIGS. 8A and 8B show the schematic cross sections of different possible pain therapy device designs. Controller (1) comprises of electronic circuitry (3), rechargeable battery (4), on/off switch (6) and an LED indicator (5). FIG. 8A illustrates the integrated design where both the controller and applicator makes a single unit. Whereas FIG. 8B illustrates the two piece design in which both the controller and applicator are two separate entities and are connected through a wire/wireless.

FIGS. 9A to 9C, FIGS. 10A and 10B, FIGS. 11A and 11B, FIGS. 12A and 12B, and FIGS. 13A and 13B illustrate schematic cross sections of different exemplary applicator designs. The applicator generally includes an ultrasound transducer (8), heat/cold transducer (10), insulation layer (9), temperature sensors (1), top cover (7) and bottom cover. In some of the embodiments this also includes side support (13). In some embodiments the ultrasonic energy from applicator is transferred into the body through conducting media. U.S. application Ser. No. 14/011,273 provides more detail about these devices, the entire disclosure of which is incorporated herein by reference.

In one example, the power source used to operate the device can be a rechargeable battery, an AC power adapter and/or a capacitor. The input power unit may be configured for delivering current of range 0.1 mA to 4000 mA and delivering potential of range 2V to 120V, to deliver multiple therapies at different currents or voltages. For example, the current and voltages used for accomplishing, heat, cold, ultrasonic and TENS energies may be different. The device can include a plurality of circuit blocks configured and connected to various transducers for converting the input energy to heat, cold and ultrasound. This section may have a switch to keep the device in on/off/standby mode to conserve energy when not in use. The standby function is optionally automated based on the program in the controller.

A controller can be provided for containing the required software for operation. The controller also interfaces with the detecting transducers for the required computation for quantifying the detected values. When various forms of energy are supplied to the treatment area via a combination effect of control signals, the controller and the transducer can supply pulses with a minimum duration of 1 millisecond or more.

The controller may be further configured/programmed for altering the outputs on the basis of the feedback signals provided by the sensors disposed over the said applicator. Based on the settings and the program running in the controller, the exact temperature and duration of application of heat or cold or electric treatment or ultrasound can be precisely controlled by this circuit block. Various durations of temperature and frequencies are possible.

The applicator can have an ultrasound sound transducer and heat and/or cold transducers or TENS electrodes. As shown in FIGS. 9A to 9C, 10A, 10B, 11A, 11B, 12A, 12B, 13A and 13B illustrate, these transducers may be aligned one above the other. In one example, the ultrasound transducer may be positioned above the heat/cold transducer, or the ultrasound transducer can surround the heat/cold transducer and vice versa, or the transducers can be side by side, or the design may be an irregular design to utilize the produced energies efficiently and treat the physiological condition very effectively.

The applicator may also have temperature sensors placed on or around the heating/cooling element to measure the temperatures and send the information to the controller through feedback loop mechanism to maintain constant exposure temperatures. The sensors can be configured for feedback control of the device. For example, the sensors can provide control signals to the controller for the optimized and efficient use of the different energies to be applied over the treatment area. The sensors (which may include ultrasonic transducers that have dual function as sensor and therapeutic agent) can provide additional information regarding blood flow, tissue thickness, blood oxygen levels, pain-pressure sensitivity, applicator contact with body and so on. This can reduce the power usage of the power source/battery and allow for prolonged use without repeated charging.

In use, a gel or other material may be positioned on a patient's skin. This may help the ultrasound, electrical stimulation and any other form of physical medicine that needs an efficient conductive media to transfer energy into the body. For example, thermal energy from ultrasound can only be transferred efficiently through a conductive (electrically or thermally or acoustically) gel, while thermal energy from superficial heating may be transferred directly into the body without including any additional conducting medium. The electrical stimulation also requires conductive gel pads to pass electric current into the body and in between the electrodes. Further the applicator may also require an adhesive tape to attach it to the body. It is also possible that the adhesive pads could act as conductive elements, or vice versa. The gel could be applied in the form of liquid, semi-solid, solid, suspension or slurry. The applicators can also be attached to the body through strap mechanism. Therefore, the applicator may come in direct contact with the body partially or fully through an additional conducting medium as required or applicator may come in contact with skin without any conductive medium, if applied therapy do not require such a medium.

In an exemplary embodiment, the method can include directing ultrasound waves at a tissue and heating the tissue with thermal energy pulses. The thermal energy pulses may be synchronized to arrive at the tissue simultaneously with the ultrasound waves within a preset range, and the heat of each thermal energy pulse can be dissipated in an environment that includes the tissue before a subsequent thermal energy pulse arrives at the tissue. The deposited heat energy per pulse, the number of pulses, and the repetition rate of the pulses may be determined by a processor according to the temperature and the heat dissipation capability of the tissue. The electrical energy can be delivered continuously or in pulses at low frequency (2-20 Hz) or high frequency (20 Hz to 200 Hz) in combination with pulsed or continuous thermoceuticals. Therefore, the above-described intelligent pain management computer systems and methods for managing pain therapy may be implemented using a variety of pain therapy devices or physical medicine delivery systems described herein.

The compact design of the disclosed device can give a patient the freedom to use the device on the move and/or at home, reducing the clinic visits. The device can be used/placed on any part of the body and also for any ailment that will respond to these energies.

To provide further explanation, the following examples are provided as additional illustrative embodiments and use cases for the computer-implemented pain management system disclosed herein.

The present disclosure provides, in one aspect, a pain therapy device for delivering at least one form of physical medicine having a microprocessor and wired/wireless networking capability that communicates with mobile or smart phones or computers either through physical connectivity or remotely (e.g., via Bluetooth or wifi) and enables users to manage and track therapeutic treatments (e.g., pain therapy). In one implementation, the application includes software that is stored on a memory of the mobile therapeutic device and is executed by the processor.

The present disclosure also provides a solution for efficiently managing pain without drugs and invasive procedures, by delivering one or more forms of physical therapies either individually, sequentially or in combination. The physical therapies are compliant and can be self-administered conveniently, safely and cost effectively. Further, the present disclosure provides a method for connecting patients with the health care providers. In some examples, it enables them to communicate the progression or regression of the therapy as they experience it along with measurable feedback, compliance data, sensor data, if any. It also allows them to receive a safe, compliant and efficient therapy.

The present disclosure also provides a method employing an intelligent means for delivering physical medicine to a plurality of patients, with an option from a remote location, comprising the steps of: (i) providing each of the patients with a personal pain therapy device(s) capable of providing one or more forms of physical medicine to patients on demand (at home or at doctor's office), (ii) providing a microprocessor associated with therapy device capable of controlling physical medicine delivery and simultaneously send and receive the information over network(s) to suggest or carry out preferred prescription(s), monitoring and compliance related activities; (iii) providing the usage information, sensing information and compiling the status report of the said therapy device(s) via a network(s); (iv) providing a quantified patient response measurement after each compliance of prescription that is transmitted to the remote computing system for a report; and (v) providing an analysis algorithm on the local or remote computing system for processing the data collected or monitored from the device, sensors, and patients for formulating an automated prescription, modifying a prescription, and assessing the therapy compliance and thereof. In a sense, the most efficacious therapy is identified akin to clinical trials, by comparing and contrasting and conducting statistical analysis of various therapy related parameters.

In one embodiment of the present disclosure, a repository database gathers and stores the information regarding individual or collective patient profiles, demographics, disease symptoms, diagnosis, prescription, sensing data, device usage/compliance and quantified response from patient and/or health care provider manually, semi-automatically, or automatically over the network. If the prescribed therapy does not lead to satisfactory results in a given time frame as indicated by the patient feedback, an analytical algorithm recommends alternate therapies involving same physical medicine with different dosages or alternate physical medicine or combination of physical therapies as defined by the rules for providing various physical therapies until the patient experiences most efficacious therapy as indicated by his/her feedback. Further, the algorithm with access to wider patient database comprising above information, can have the ability to compare the pain symptoms or diagnosis or profile or demographics of the patient to be treated with those in the database and thereby identify the best possible prescription(s) or dosage of physical medicine such that the therapy administered can lead to efficacious therapy.

In another embodiment of the present disclosure, the pain therapy device provided is a wearable pain therapy device that is compact, convenient, and is capable of providing a combination of physical medicine for efficacious and sustainable pain relief.

In another embodiment of the present disclosure, the disclosed system intelligently personalizes pain therapy by electronically connecting the pain therapy device to a physician computing device, enabling the health care provider to receive and view the feedback from the patient seamlessly and search a network-based database comprising data on numerous pain patients along with their patient profiles (i.e. indicating patient demographic and other information), physiological responses to the therapies, and pain relief scores received in response to the various physical medicine therapies administered. The disclosed system thereby allows the physician to identify data/statistics driven preferred therapeutic options for personalizing the pain therapy. The system provides reports and/or graphs of the recorded data such that the compliance and progression of the therapy is monitored, trends are identified, prescription rules are framed or the outcome of the therapy is correlated with the therapy or therapies administered in conjunction with multiple patient profiles with related symptoms, therapies, patient feedback, diagnosis and/or sensing data such as vital signs, tissue temperature, blood flow in painful part of the body etc. for further evaluation.

In another embodiment, the present disclosure provides a software application (e.g., a mobile application or other program that is executable by a portable device having a processor) that includes a therapy tracking feature that enables patients to record and review various parameter data related to applied pain management therapies. The parameters may include testable and quantitatively measurable aspects of certain symptoms associated with the therapy. For example, a symptom of pain may be recorded on a recurring basis (e.g., daily) by the patient ranking the extent of the pain on a fixed scale, such as 0 (for no pain) to 10 (severe pain) or 0 (no pain) to 5 (severe pain) as defined (one could also use painful and smiley faces as a graphical user interface to quantify the pain). The disclosed software application can provide reports and/or graphs of the recorded data such that trends may be identified, or such that the outcome of the therapy is correlated with the therapy or therapies administered in conjunction with the patient profile and/or physiological data such as vital signs, tissue temperature, blood flow, blood oxygen level, tissue thickness, tissue imaging etc. for further evaluation. Some of the parametric values graphed/tabulated or stored include, level of compliance, progression/regression of the therapy, patient profile, demographics, physical modality/dosage administered, and physiological data captured from sensors.

The progression or regression of the pain management therapy may be tracked in response to the historical data being requested; such tracking may include retrieving at least one of the parameters from the repository, and displaying the retrieved parameter in a tabular and/or graphical format. The tracking of pain management therapy progress and on demand/automated prescription or suggestion options can be tailored (e.g., made compliant with any governing law). In some embodiments, the patient can request the prescription and the history related to his/her treatment can also be revealed/shared with the patient.

In another embodiment of the present disclosure, the software application includes a calendar/timing feature for scheduling administrations of the pain management therapy treatments and/or appointments, or ensuring the compliance of the prescription provided. For example, if treatment involves administration of a pain management therapy on a recurring basis, and the calendar feature allows the patient to schedule such administrations and may include reminders. Similarly, if the patient does not follow the prescription or misses a dosage, the event can be recorded and evaluated as part of the comprehensive therapy review by the physician.

In another embodiment of the present disclosure, the software application provides information related to the pain management therapy and/or ongoing treatments, which is viewable on the communicating device. The information may include news, company alerts, and/or the parameters related to the therapy outcome. In some embodiments, the information is received on demand remotely or stored in the memory. For example, each of the news items may include a news story and/or a company alert. The said method may also include communicating, through the network interface, one or more messages between the patient and a case manager. Any one of the messages may be an address change notification, an insurance notification, and/or a vacation notification.

In yet another embodiment of the present disclosure, the software application provides a support feature that enables the user to communicate with, for example, a health care provider, a physician or care manager or head nurse. In other examples, the user may use the support feature to select a care manager from a list of service providers to ask questions related to the pain management therapy, and/or to request scheduling appointments and other support services.

According to another embodiment of the present disclosure, a system for managing therapeutic treatment of a disease of a patient by a user is provided, including a communicating device having a processor and a memory coupled to the processor. The said communicating device is constructed and adapted to communicate with at least one server. A software application is stored on the memory. The software application is executable by the processor and comprises a physiological data collection engine for collecting physiological data, a data storage module for storing one or more parameters related to the treatment, a tracking module for tracking the parameters, a therapy analysis engine for determining a personalized pain management therapy, and a server system interface engine for communicating information related to the treatment with a health physician, a company, and/or a case manager. In some embodiments, the communicating device may be a smart phone having a wireless network device, or a personal digital assistant having a wireless network device or a computer. The information may include news, company alerts, and/or the parameters related to therapy outcome.

The parameters and/or the information are optionally displayed to the user in an interface of the computing device. The software application may also include a calendar module for scheduling treatment administrations and/or appointments. The information may include the treatment administrations and/or the appointments.

The parameters may further include parameter data acquired from a medical test and diagnosis of the patient. The parameters may include a parameter type, a parameter value, and/or a test date. The parameter type may involve various types of pain symptom such as somatic pain, neuropathic pain, musculoskeletal pains of various body parts, back pain, arthritis (rheumatoid or osteo), elbow pain, bursitis, tendonitis, migraine, headaches, fibromyalgia, postoperative pain, joint pain, tunnel syndrome, tendon or ligament pain, acute injuries; extensibility of collagen tissue, skin lift, skin rejuvenation, facial tightening, decreases in joint stiffness, improvement in range of motion, relief in muscle spasms, increase in global and local blood flow, global and local blood oxygen levels, body/skin temperature, tissue temperature, heart rate, tenderness of the tissue (as measured by algometry), skin pH, vital signs such as blood pressure, body temperature, local metabolism, nerve conduction velocities and so on.

In another embodiment of the present disclosure, the repository database in a server system stores patient profile. The patient profile may include patient information comprising a patient name, demographics, vital signs, patient street address, a patient telephone number, time and date of therapy administration, therapy compliance, and/or a patient e-mail address. The server system may generate the messages based on the patient profile, the case manager, and/or a message type. The message type may be an address change notification, an insurance notification, and/or a vacation notification.

In another embodiment of the present disclosure, the repository database at the server system stores various physical therapies administered, the dosage, such as electric stimulation applied (voltage, current, pulsing time, duration), ultrasound (frequency, intensity, duty cycle, duration), heat (temperature, 25-50° C., duration, pulsing), cold (0-25° C., duration, pulsing), and combinations involving simultaneous and sequential applications of aforementioned physical therapies with the corresponding parameters that define the physical medicine dosage, exposure intensity, therapy duration.

In another embodiment of the present disclosure, a system and method are provided that enable entry of the patient profile, pain symptom, and prescription for physical medicine to be administered. The entered information is stored in a database for immediate or future reference to personalize the therapy.

In another embodiment of the present disclosure, a system and method are provided which enable a single device with the capability of delivering more than one physical medicine or modalities or combination of medical devices to deliver multiple physical modalities to targeted tissue such as temperature (heat or cold), ultrasound (e.g., 1 or 3 MHz) and electrical stimulation (e.g., TENS) to a targeted live tissue to provide optimum therapeutic benefits. Further, the system may have the capability collect non-invasive sensing information of patient such as vital signs, tissue thickness, tissue images, tissue temperature at different depths, blood flow rates in the skin or in the tissue, blood oxygen levels, pressure point depth or pressure-pain threshold, and skin pH, if required. In addition, the system may be configured for retrieving and storing treatment information (including day and time), subject information, sensing information, demographics, billing information and outcome of the therapy session as defined by the subject on a given pain relief score from unsatisfactory to fully satisfied and further capable of communicating with a database located on a server either locally or in cloud.

In another embodiment of the present disclosure, a system and method are provided which are configured to perform analysis of the compiled or stored data to determine whether the prescribed treatment is compliant, progressing or regressing or needs alteration. The system and method may be designed in such a way that it conducts comprehensive analytics regularly on ever increasing data being gathered and intelligently refines its recommendation for prescription or automatically titrates the physical medicine delivery/ prescription. It may normalize the pain relief score from multitude of patients and may make recommendations for personalized physical medicine, i.e., individual or combination modalities, method, dosage and therapy duration, for individuals or a group or section of demographics and may generate automatic messages regarding pain therapy status.

In another embodiment of the present disclosure, a graphical user interface for the entry of data (i.e., prior to the treatment) is provided, such as patient profile, demographics, symptoms, diagnosis, pre-existing condition. Further, the interface may display information correlating pertinent entry data in a graphical manner, to show the relationship between individual (or a group of) patient profile(s) or demographics, with regard to physical medicine(s) administered and the outcome of the therapy, risk and benefit ratios with respect to any type of clinical application or therapy as warranted to make the therapy safe, personable and efficient.

The disclosed graphical user interface can also display the population exposures and outcomes, costs and benefits, antecedents and outcomes, causes and effects, and comorbidities of any number of health care scenarios. The graphical user interface can provide a graphical representation of the relationship between any such information or events.

In another embodiment of the present disclosure, a computer readable medium is provided for storing executable instructions for execution by a computer having memory, where medium stores instructions for inputting contact information into a data storage device, transmitting an electronic message based on the contact information, receiving a response, storing the response and a timestamp into the data storage device, storing a time and date of receipt of the response into the data storage device, and querying the database for trends based on the response.

In some embodiments, the ever increasing amount of information stored in the database with regard to patient profiles, pain symptoms, physical therapies administered, outcomes measured, sensing data gathered, compliance levels monitored would be collectively and intelligently evaluated to propose/recommend a preferred prescription either automatically or upon request to personalize the pain therapy for an individual or classified group. The disclosed system is capable of self-correcting/fine tuning the prescription recommendation or optimizing the physical medicine delivery as the data sampling size increases from a broad spectrum of the society.

In another embodiment of the present disclosure, a medical device is provided which is capable of delivering multiple modes of physical medicine (e.g., electric stimulation, ultrasound, heat and cold either individually or in combination), collecting non-invasive sensing information relevant to assessing the progression or regression of the therapy, connects wirelessly to a database, and transmits the entry data, therapy data, sensing data and the patient feedback, conducts analytics, identifies the trends/correlations, and thereby intelligently recommends the prescription or automatically administers the therapy.

In another embodiment, a portable and versatile pain therapy device is presented that provides an applicator, a plurality of sensors and an electronic controller powered by a rechargeable battery/power source. The said device is capable of producing and applying different forms of energies when placed on the treatment area (the skin). The generated energies penetrate through the skin into the deeper layers to produce soothing and palliative effects to give the sense of relief.

In another embodiment, disclosed is provided a pain therapy device, comprising: an applicator and a controller wherein the applicator is configured for accepting at least one electrical input; a controller configured for providing the intensity, sequence, nature, and timing information for the different energies supplied to the said applicator; and the applicator comprising of plurality of transducers configured for converting input electrical energy to different forms of output energies that are transmitted to the dermal and sub-dermal layers; and a plurality of sensors disposed over the applicator configured for providing a feedback control signal to the controller.

Further herein disclosed is a method for performing electronic therapy using a portable electronic device comprising the steps of: attaching the device to the skin of the subject; inputting electrical energy from a power source; controlling the electrical energy power input using a controller; converting the electrical energy to different forms of output energy using a plurality of configured circuit blocks; and providing the intensity, sequence, nature, and timing signals for activating therapy using different energies or at least one energy through an applicator; and modifying the intensity, sequence, nature, and timing signals as per the feedback control signals from a plurality of sensors.

In a further embodiment of the present invention there is provided a feedback control mechanism enabled by a plurality of sensors disposed over the applicator, which provides further control over the application of the different energies to the treatment area.

The sensors can collect and send the data to the feedback control mechanism of the controller to control various parameters such as temperature, frequency, intensity, input power, time, or any other parameters. The data collected can be sent to the feedback loop of the controller. In another example, the data collected can be delivered as outlined above with respect to the intelligent pain management system described.

The following embodiments provide additional examples for the features described above.

1. An improved method for providing physical medicine to a plurality of patient(s), with an option for connected care, comprises the steps of: a) providing each of the patient(s) with a microprocessor based pain therapy device(s) capable of providing one or more forms of physical medicine to patient(s) on demand; b) providing the therapy device the capability to accept input and process information or commands from the user to store the information and to execute the device functionality or operation; c) providing the therapy device with a sensor(s) capable of sensing at least one parameter related to various functional aspects of human body and the therapy device; d) providing the therapy device with the capability of wired/wireless connectivity for sending and receiving information and commands over network(s).

2. A method for providing physical medicine to a patient as described in [1], wherein the personal pain therapy device(s) includes a unique identification number allotted by the manufacturer and is associated with a unique identity number of a single or multiple patients.

3. A method of providing physical medicine as described in [1], wherein physical medicine delivered includes thermoceuticals (temperature application based therapies including ultrasound and infrared based therapies) or electroceuticals (electric current and voltage application based therapies) or alike or combinations thereof.

4. A method of providing physical medicine as described in [1], wherein the information is communicated to a software application directly or through an electronic device, where the information transmitted includes the patient profile, and any other pertinent information that is either entered, stored or collected prior to or during or post therapy administration.

5. A method of providing physical medicine as described in [4], wherein the information includes, a) the compliance information regarding the administration of therapy (e.g., time, date, and device usage related parameters). b) the information from sensor(s) such as vital signs or body tissue density or thickness, blood flow rate (at painful part of the body), blood oxygen levels, body temperature or skin temperature or tissue temperatures, and pressure-pain threshold measurements. c) quantified patient response or feedback after each qualified therapy session.

6. A method of providing physical medicine as described in [1], wherein a device gathers and stores information comprising of compliance, information from sensor and the patient feedback (in response to the therapy administered), manually, semi-automatically, or automatically over the network into a repository for the patient.

7. A method of providing physical medicine as described in [1], wherein an analytical algorithm identifies an efficacious and personalized therapy by conducting analytics on the repository data, and wherein the data on patient profiles, demographics, vital signs, disease symptom, sensing information received from the therapy device, physical medicine modality, method, dosage and intensity administered for a given symptom and its compliance and patient feedback on the outcome of given therapy is analyzed, correlated and rank ordered.

8. A method of providing physical medicine as described in [1], wherein a repository database is analyzed using an algorithm to identify optimal efficacious therapy for a given symptom (e.g., back pain vs. knee pain) or for a given patient profile or demographics or for any given physical medicine or combination thereof.

9. A method of providing physical medicine as described [1], wherein a repository database uses an algorithm to automatically identify a prescription or modify a prescription or deliver an optimal physical medicine(s) safely for a given patient profile (e.g., age, sex, body mass index) and symptom (e.g., acute pain, back pain, arthritis, fibromyalgia) or combination thereof.

10. A repository database as described [6] compiles the information and present the status reports graphically or in tabular form to monitor the progression or regression of the therapy and compare the given patient's therapy outcome with that of others who have a similar or related symptom, or received a similar or related therapy or have a similar or related profile or received a similar or related physical medicine.

11. A method for providing physical medicine to a patient as described in [1], wherein compiling the status report of the said therapy device(s) via a network(s) includes storing of the aforesaid information into a repository that includes: storing the device usage data; storing the measurements from sensor data (collected from patients); storing the profile and contact information of the patients; storing the disease symptom of the patients; storing the prescription, diagnosis data and the rules associated with said prescription; storing the prescription provider data associated with each prescription; storing the compliance data associated with each prescription; and storing the quantified patient response measurement after each therapy session.

12. As described in [1], the method for receiving the information or commands or alerts to the therapy device from a remote device or location or software application includes: a) a method of delivering the prescription and administering the therapy b) A method for controlling the device functions such as switch on or off, lock or unlock the usage of the device, prohibit or restrict or enable the device usage features c) A method for delivering alerts or news feeds under certain conditions.

13. A method for providing physical medicine to a patient as described in [1], wherein compiling the status report of the said therapy device(s) via network(s) further includes steps of: storing information related to a condition of the patient when the alert is communicated, storing information related to the therapy being delivered when the alert is communicated; storing information related to the alert when the alert is communicated, analyzing the stored patient condition (progression or regression) information, the therapy delivery information and the alert information; and reporting the analyzed information to the prescription provider.

14. A method for providing physical medicine to a patient as described in [1], wherein the method further includes these steps: monitoring of information related to input information associated with the specific patient; and comparing the monitored/stored information with at least one rule of prescription; to automate the optimal therapy required or to alert the patient and the prescription provider simultaneously if a prescription rule is violated or optimal therapy is not accomplished.

15. A method for providing physical medicine to a patient as described in [1], wherein the information corresponds to an attribute of the portable personal therapy device(s), the attribute selected from the group consisting of: patient information, physician information, control information; medicament information, and location information.

16. A method for providing physical medicine to a patient as described in [1], wherein the delivery of physical medicine is adjusted based on non-invasive sensing data such as vital signs or tissue density or thickness, blood flow rate, blood oxygen levels, skin temperature or tissue temperatures, pressure-pain threshold (algometer) measurements, and the patient feedback on comfort or discomfort levels.

17. A method for providing physical medicine to a patient as described in [1], wherein the physical medicine is automatically delivered by comparing or correlating patient profile or demographics and symptoms with a database of reports comprising the best therapy outcomes under similar conditions.

18. A method for providing physical medicine to a patient as described in claim [1], wherein the information corresponds to an event that is tracked by the therapy device, the event selected from the group consisting of: power events (charging or discharging or power supply levels); alarm events (therapy progress or deviations); alert events (violation of prescription or safety concerns); maintenance events; therapy events (timing, dosage, prescription compliance); and custom events (device performance, maintenance, activation, deactivation and any rules that ensure the safe operation of the device).

19. An Intelligent Pain Management System that receives patient's feedback in the form of pain score from any pain therapy device(s) that deliver physical medicine comprises of: a) a communication system that recognizes and configures a therapy device(s) to provide two way wired/wireless transmission of information over the network; b) a plurality of portable therapy device(s), each having a processor and a memory associated with each processor for storing programs for operating the processor to control the therapy device, including the means of monitoring and communication; c) a system that accepts patient(s) information as an input, and integrates with the therapy device(s) to enable communication, transfer and receive pertinent data d) the therapy device(s) connected to an external electronic mobile device or computing device with at least one remote server to access a repository database comprising of at least one prescription rule and at least one patient data, and also configured to record and monitor activity of the therapy device and operating commands through associated program(s); e) a system that communicates information to the server and compares the communicated information to information stored in the database of at least one prescription rule and at least one patient data to determine if the communicated information falls within a range of values indicated as acceptable by at least one prescription rule; and accordingly provides alerting information to the patient and prescription provider simultaneously.

20. A kit for providing physical medicine to a patient comprising an electronic controller and applicator, optionally including sensors for vital signs or for imaging and measuring the depth of tissue, or for measuring skin or tissue or deep tissue temperature, or sensors for measuring blood flow or for measuring blood oxygen ultrasound transducers; electrodes; thermoelectric elements; a microprocessor and software that controls the device operations; and/or network enabled devices.

Numerous specific details are set forth herein to provide a thorough understanding of the claimed subject matter. However, those skilled in the art will understand that the claimed subject matter may be practiced without these specific details. In other instances, methods, apparatuses, or systems that would be known by one of ordinary skill have not been described in detail so as not to obscure claimed subject matter.

Unless specifically stated otherwise, it is appreciated that throughout this specification discussions utilizing terms such as "processing," "computing," "calculating," "determining," and "identifying" or the like refer to actions or processes of a computing device, such as one or more computers or a similar electronic computing device or devices, that manipulate or transform data represented as physical electronic or magnetic quantities within memories, registers, or other information storage devices, transmission devices, or display devices of the computing platform.

The system or systems discussed herein are not limited to any particular hardware architecture or configuration. A computing device can include any suitable arrangement of components that provides a result conditioned on one or more inputs. Suitable computing devices include multipurpose microprocessor-based computer systems accessing stored software that programs or configures the computing system from a general purpose computing apparatus to a specialized computing apparatus implementing one or more embodiments of the present subject matter. Any suitable programming, scripting, or other type of language or combinations of languages may be used to implement the teachings contained herein in software to be used in programming or configuring a computing device.

Embodiments of the methods disclosed herein may be performed in the operation of such computing devices. The order of the blocks presented in the examples above can be varied—for example, blocks can be re-ordered, combined, and/or broken into sub-blocks. Certain blocks or processes can be performed in parallel.

The use of "adapted to" or "configured to" herein is meant as open and inclusive language that does not foreclose devices adapted to or configured to perform additional tasks or steps. Additionally, the use of "based on" is meant to be open and inclusive, in that a process, step, calculation, or other action "based on" one or more recited conditions or values may, in practice, be based on additional conditions or values beyond those recited. Headings, lists, and numbering included herein are for ease of explanation only and are not meant to be limiting.

While the present subject matter has been described in detail with respect to specific embodiments thereof, it will be appreciated that those skilled in the art, upon attaining an understanding of the foregoing, may readily produce alterations to, variations of, and equivalents to such embodiments. Accordingly, it should be understood that the present disclosure has been presented for purposes of example rather than limitation, and does not preclude inclusion of such modifications, variations, and/or additions to the present subject matter as would be readily apparent to one of ordinary skill in the art.

The invention claimed is:

1. A system, comprising:
    a patient analytics database comprising, for each prior patient of a plurality of prior patients, a profile comprising demographic data and physiological measurements correlated with an applied pain management therapy and an outcome comprising either satisfactory or unsatisfactory; and
    a pain therapy device communicatively coupled to the patient analytics database, the pain therapy device comprising:
        an applicator comprising a thermoelectric element, an ultrasound transducer, and an electrode component;
        a plurality of physiological sensors;
        a processor; and
        a memory communicatively coupled to the processor and comprising instructions configured to be executed by the processor, wherein the processor is configured to receive the instructions from the memory and to execute the instructions to perform operations comprising:
            accessing, for a new patient, new patient demographic data and a new patient initial pain score;
            receiving new patient physiological measurements from the plurality of physiological sensors;
            receiving, from the patient analytics database, a pain management therapy for the new patient, the pain management therapy comprising (i) a thermoelectric parameter that controls a temperature of the thermoelectric element, (ii) an ultrasound parameter that controls ultrasound output by the ultrasound transducer, or (iii) an electrode parameter that controls electrical output by the electrode component, wherein the pain management therapy is determined by identifying a reference profile comprising an outcome identified as satisfactory and one of: (i) demographic data matching the new patient demographic data or (ii) physiological data matching the new patient physiological measurements;
            applying the pain management therapy to the new patient via the applicator by applying one or more of the thermoelectric parameter, the ultrasound parameter, or the electrode parameter to the applicator;
            responsive to determining that the pain management therapy is complete, receiving, from the pain therapy device, an updated pain score for the new patient; and
            storing, in the patient analytics database, a new patient profile comprising the demographic data for the new patient, the initial pain score, the updated pain score, and the new patient physiological measurements.

2. The system of claim 1, the operations further comprising:
    determining an indication of reduced pain for the new patient by determining that the updated pain score is lower than the initial pain score by a threshold amount; and
    updating the new profile in the patient analytics database with the indication and marking the new profile as a successful treatment.

3. The system of claim 1, wherein the physiological measurements comprise: a vital sign of the patient, a local body temperature of the patient, a local tissue temperature of the patient, a local blood flow rate of the patient, a local blood oxygen level of the patient, a local body tissue thickness of the patient, or a local body tissue density of the patient.

4. The system of claim 1, wherein the pain therapy device further comprises a user input device, and wherein the initial pain score and the updated pain score are received via the input device.

5. The system of claim 1, wherein the pain therapy device further comprises:
- a heat switch and a cold switch communicatively coupled to the processor and configured to control the thermoelectric element based on the thermoelectric parameter;
- an ultrasound switch, an ultrasound intensity control, and an ultrasound duty cycle communicatively coupled to the processor;
- an ultrasound power amplifier communicatively coupled to the ultrasound switch, the ultrasound intensity control, and the ultrasound duty cycle, the ultrasound power amplifier configured to drive the ultrasound transducer based on the ultrasound parameter; and
- an electric stimulation switch communicatively coupled to the processor and an electric stimulation circuit communicatively coupled to the electric stimulation switch, the electric stimulation circuit configured to drive the electrode component based on the electrode parameter.

6. The system of claim 5, wherein the thermoelectric parameter is configured to set the heat switch and the cold switch.

7. The system of claim 5, wherein the ultrasound parameter is configured to set the ultrasound switch, the ultrasound intensity control, and the ultrasound duty cycle.

8. The system of claim 5, wherein the electrode parameter is configured to set the electric stimulation switch.

9. The system of claim 1, wherein the plurality of physiological sensors comprise a temperature sensor, a blood flow sensor, an oxygen sensor, and a tissue thickness sensor.

10. The system of claim 1, wherein the operations further comprise:
- determining an indication that the pain therapy is not satisfactory by determining that the updated pain score is not less than the initial pain score by a threshold;
- updating the new patient profile in the patient analytics database with the indication;
- receiving, from the patient analytics database, an updated pain management therapy comprising (i) an updated thermoelectric parameter, (ii) an updated ultrasound parameter, or (iii) an updated electrode parameter, wherein the updated pain management therapy is determined by identifying, in the patient analytics database, an additional reference profile comprising an outcome identified as satisfactory and (i) demographic data matching the new patient demographic data or (ii) physiological data matching the new patient physiological measurements; and
- titrating the pain management therapy by applying the (i) updated thermoelectric parameter, (ii) the updated ultrasound parameter, or (iii) the updated electrode parameter to the applicator.

11. The system of claim 10, wherein titrating the pain management therapy for the patient comprises adjusting a duration corresponding to at least one of the thermoelectric parameter, the ultrasound parameter, or the electrode parameter.

12. The system of claim 1, wherein demographic data comprises (i) an age range, (ii) a gender, (iii) a body mass index, or (iv) a pre-existing medical condition.

13. The system of claim 1, the operations further comprising receiving a new patient pain type comprising one of (i) acute pain, (ii) chronic pain, or (iii) musculoskeletal pain, wherein each profile of the plurality of profiles further comprises a pain type and wherein the reference profile comprises a pain type identical to the new patient pain type.

14. The system of claim 1, wherein identifying the reference profile is performed by a server device.

* * * * *